United States Patent
Chassagne et al.

(10) Patent No.: US 10,005,807 B2
(45) Date of Patent: Jun. 26, 2018

(54) SYNTHESIS OF SIALYLATED/FUCOSYLATED HUMAN MILK OLIGOSACCHARIDES

(71) Applicant: GLYCOM A/S, Hørsholm (DK)

(72) Inventors: Pierre Chassagne, Beaumont (FR); Nikolay Khanzhin, Humlebaek (DK); Markus Jondelius Hederos, Trelleborg (SE); Elise Champion, Toulouse (FR); Martin Matwiejuk, Hamburg (DE); Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 26 days.

(21) Appl. No.: 14/783,783

(22) PCT Filed: Apr. 11, 2014

(86) PCT No.: PCT/IB2014/060648
§ 371 (c)(1),
(2) Date: Oct. 9, 2015

(87) PCT Pub. No.: WO2014/167538
PCT Pub. Date: Oct. 16, 2014

(65) Prior Publication Data
US 2016/0075729 A1 Mar. 17, 2016

(30) Foreign Application Priority Data
Apr. 12, 2013 (GB) .................................... 1306689.9

(51) Int. Cl.
*C07H 5/04* (2006.01)
*C07H 1/00* (2006.01)

(52) U.S. Cl.
CPC ................. *C07H 5/04* (2013.01); *C07H 1/00* (2013.01)

(58) Field of Classification Search
None
See application file for complete search history.

(56) References Cited

U.S. PATENT DOCUMENTS

| | | | | |
|---|---|---|---|---|
| 2014/0046044 A1* | 2/2014 | Perez Figueroa | ........ | C07H 3/06 536/17.1 |
| 2014/0248415 A1* | 9/2014 | Brassart | ................. | C07H 7/027 426/658 |
| 2014/0323705 A1* | 10/2014 | Hederos | .................... | C07H 1/00 536/17.2 |

FOREIGN PATENT DOCUMENTS

| | | |
|---|---|---|
| WO | 2011/100979 | 8/2011 |
| WO | 2011/130332 | 10/2011 |
| WO | 2012/007588 | 1/2012 |
| WO | 2012/106665 | 8/2012 |
| WO | 2012/113404 | 8/2012 |
| WO | 2012/127410 | 9/2012 |
| WO | 2012/155916 | 11/2012 |
| WO | 2012/156897 | 11/2012 |
| WO | 2012/156898 | 11/2012 |

OTHER PUBLICATIONS

Hotta, K., Komba, S., Ishida, H., Kiso, M., & Hasegawa, A. (1994). Synthetic studies on sialoglycoconjugates 61: Synthesis of α-series ganglioside GM1α. Journal of carbohydrate chemistry, 13(5), 665-677.*

Lay, L., Panza, L., Russo, G., Colombo, D., Ronchetti, F., Adobati, E., & Canevari, S. (1995). Oligosaccharides related to tumor-associate antigens. Part 3. Synthesis of the propyl glycosides of the trisaccharide β-D-Galp-(1→ 3)-β-D-GalpNAc-(1→ 3)-α-D-Galp and of the Tetrasaccharide α-L-Fucp-(1→ 2)-β-D-Galp-(1→ 3)-β-D-GalpNAc-(1→ 3)-α-D-Galp, compo.*

Murase, T., Kameyama, A., Kartha, K. P. R., Ishida, H., Kiso, M., & Hasegawa, A. (1989). Journal of Carbohydrate Chemistry, 8(2), 265-283. (Year: 1989).*

Hasegawa, A., Nagahama, T., & Kiso, M. (1992). Carbohydrate research, 235, C13-C17. (Year: 1992).*

International Search Report and Written Opinion dated Jul. 9, 2014 in corresponding International Patent Application No. PCT/IB2014/060648.

Stinabritt Nilsson et al., "Synthesis of Two Tumor-Associated Oligosaccharides: Di-and Trifucosylated Para-Lacto-N-Hexaose," J. Carbohydrate Chemistry, vol. 10, No. 6, pp. 1023-1048 (1991).

L.M. Likhosherstov et al., "Synthesis of N-glycol-β-glycopyranosylamines, human milk fucooligosaccharide derivates," Russian Chemical Bulletin, International Edition, vol. 61, No. 9, pp. 1816-1821 (Sep. 2012).

Evelyn Jantscher-Krenn et al., "The human milk oligosaccharide disialyllacto-N-tetraose prevents necrotising enterocolitis in neonatal rats," Gut, pp. 1-9 (Dec. 3, 2011).

Sharron G. Penn et al., "Fragmentation behavior of multiple-metal-coordinated acidic oligosaccharides studied by matrix-assisted laser desorption ionization Fourier transform mass spectrometry," International Journal of Mass Spectrometry, vol. 195/196, pp. 259-269 (2000).

Galina V. Pazynina et al., "Synthesis of complex α2-3 sialooligosaccharides, including sulfated and fucosylated ones, using Neu5Acα2-3Gal as a building block," Mendeleev Commun., vol. 13, No. 6, pp. 245-248 (2003).

(Continued)

*Primary Examiner* — Shaojia A Jiang
*Assistant Examiner* — Dale R Miller
(74) *Attorney, Agent, or Firm* — Neal, Gerber & Eisenberg LLP

(57) ABSTRACT

An achemo-enzymatic synthesis of oligosaccharides of formula 1 is presented wherein R is selected from —OH, —N 3 and —OR 6 wherein R 6 is selected from allyl optionally substituted by one or more methyl, propargyl optionally substituted by one or more methyl, 2-trimethylsilyl-ethyl, —(CH 2) n —NH 2 and —(CH 2) n —N 3 wherein integer n is to 10, preferably 2 or 3, R is selected from sialyl moiety, —SO 3 H and —CH(R)—COOH wherein R is selected from H, alkyl and benzyl, R 2 is selected from H and fucosyl, R 3 is selected from H and sialyl, R 4 is selected from H and fucosyl, provided that at least one of R 3 and R 4 is H, and A is a divalent carbohydrate linker, having important biological activities and significant commercial value for the pharmaceutical and food industry.

14 Claims, No Drawings

(56) References Cited

OTHER PUBLICATIONS

Vince Pozsgay et al., "Synthesis of a Tetrasaccharide Building Block of the O-Specific Polysaccharide of *Shigella dysenteriae* Type 1," Tetrahedron, vol. 48, No. 47, pp. 10249-10264 (1992).
Hai Yun et al., "Synthetic Disialyl Hexasaccharides Protect Neonatal Rats from Necrotizing Enterocolitis," Angew. Chem. Int. Ed., vol. 53, pp. 6687-6691 (2014).
Helen Attrill et al., "The structure of siglec-7 in complex with sialosides: leads for rational structure-based inhibitor design," Biochem. J., vol. 397, pp. 271-278 (2006).
Anirban Bhunia et al., "Consistent Bioactive Conformation of the Neu5Acα(2—>3)Gal Epitope Upon Lectin Binding," ChemBioChem, vol. 9, pp. 2941-2945 (2008).
Gerard Strecker et al., "Assignment of the $^1$H- and $^{13}$C-NMR Spectra of Eight Oligosaccharides of the Lacto-N-tetraose and Neotetraose Series," Glycoconjugate J., vol. 6, pp. 67-83 (1989).
Jie Xia et al., "An Efficient Synthesis of Two Monosulfated Trisaccharides with the Galβ1,3GlcNAcβ1,3Galβ-0-Allyl Backbone," Bioorganic & Medicinal Chemistry Letters, vol. 9, pp. 2941-2946 (1999).
Mohamed R.E. Aly et al., "Synthesis of lacto-N-neotetraose and lacto-N-tetraose using the dimethylmaleoyl group as amino protective group," Carbohydrate Research, vol. 316, pp. 121-132 (1999).
Takayuki Ando et al., "First total synthesis of α-(—>3)/a-(2—>6)-disialyl lactotetraosyl ceramide and disialyl Lewis A ganglioside as cancer-assocated carbohydrate antigens," Carbohydrate Research, vol. 338, pp. 503-514 (2003).
Dino K. Ress et al., "Sialic Acid Donors: Chemical Synthesis and Glycosylation," Current Organic Synthesis, vol. 1, pp. 31-46 (2004).
Rosalia Agusti et al., "Lactose derivatives are inhibitors of *Trypanosoma cruzi* trans-sialidase activity toward conventional substrates in vitro and in vivo," Glycobiology, vol. 14, No. 7, pp. 659-670 (2004).
Tadasu Urashima et al., "Nutrition and Diet Research Progress: Milk Oligosaccharides," Nova Biomedical Books, New York, 99 pages. (2011).
Vishwanath B. Chachadi et al., "Exquisite binding specificity of *Sclerotium rolfsii* lectin toward TF-related O-linked mucin-type glycans," Glycoconj J., vol. 28, pp. 49-56 (2011).
Oliver Schwardt et al., "Examination of the Biological Role of the α(2—>6)-Linked Sialic Acid in Gangliosides Binding to the Myelin-Assocaited Glycoprotein (MAG)," J. Med. Chem., vol. 52, pp. 989-1004 (2009).
Gastón Paris et al., "A Sialidase Mutant Displaying trans-Sialidase Activity," J. Mol. Biol., pp. 345, pp. 923-934 (2005).
Subramaniam Sabesan et al., "Combined Chemical and Enzymatic Synthesis of Sialyloligosaccharides and Characterization by 500-MHz $^1$H and $^{13}$C NMR Spectroscopy," J. Am. Chem. Soc., vol. 108, pp. 2068-2080 (1986).
Hsin-Yu Liao et al., "Differential Receptor Binding Affinities of Influenza Hemagglutinins on Glycan Arrays," J. Am. Chem. Soc., vol. 132, pp. 14849-14856 (2010).
Takayuki Ando et al., "A Highly Efficient Synthetic Route to β(2—>3)/α(2—>6) Disialyl Lewis A as a Cancer Associated Carbohydrate Antigen[1]," J. Carbohydrate Chemistry, vol. 20, No. 5, pp. 425-430 (2001).
Karl Jansson et al., "2-(Trimethylsilyl)ethyl Glycosides,[1] Synthesis, Anomeric Deblocking, and Transformation into 1,2-Trans [1]-0-Acyl Sugars," J. Org. Chem., vol. 53, pp. 5629-5647 (1988).
Stephen F. Altschul et al., "Gapped BLAST and PSI-BLAST: a new generation of protein database search programs," Nucleic Acids Research, vol. 25, No. 17, pp. 3389-3402 (1997).
Björn Neubacher et al., Preparation of sialylated oligosaccharides employing recombinant trans-sialidase from *Trypanosoma cruzi*, Org. Biomol. Chem., vol. 3, pp. 1551-1556 (2005).
Samuel Karlin et al., "Applications and statistics for multiple high-scoring segments in molecular sequences," Proc. Natl. Acad, Sci. US, vol. 90, pp. 5873-5877 (Jun. 1993).
Xi Chen et al., "Advances in the Biology and Chemistry of Sialic Acids," ACS Chemical Biology, vol. 5, No. 2, pp. 163-176 (2010).
George Osanjo et al., "Directed Evolution of the α-L-Fucosidase from *Thermotoga maritime* into an α-L-Transfucosidase," Biochemistry, vol. 46, pp. 1022-1033 (2007).
Cheng-Chi Wang et al., "Glycans on influenza hemagglutinin affect receptor binding and immune response," PNAS, vol. 106, No. 43, pp. 18137-18142 (Oct. 27, 2009).

\* cited by examiner

SYNTHESIS OF SIALYLATED/FUCOSYLATED HUMAN MILK OLIGOSACCHARIDES

CROSS REFERENCE TO RELATED APPLICATIONS

This application is the National Phase entry of PCT/IB2014/060648, which claims priority to Great Britain Patent Application No. 1306689.9, filed Apr. 12, 2013. The content of these applications is incorporated herein by reference in their entirety.

FIELD OF THE INVENTION

The invention relates to a chemo-enzymatic synthesis of sialylated and optionally fucosylated human milk oligosaccharides (HMOs) and their analogs having commercial value for the pharmaceutical and food industry.

BACKGROUND OF THE INVENTION

In recent years, the manufacture and commercialization of complex carbohydrates, particularly secreted oligosaccharides, have increased significantly due to their roles in numerous biological processes occurring in living organisms. Secreted oligosaccharides such as human milk oligosaccharides (HMOs), mucin oligosaccharides and Lewis type oligosaccharides have gained much interest and have become important commercial targets for nutrition and therapeutic applications. In particular, the synthesis of these oligosaccharides has increased significantly due to their role in numerous biological processes occurring in humans.

Many human milk oligosaccharides contain sialosides, mainly N-acetyl-neuraminic acid, that is most frequently found in the terminal end of oligosaccharides. The linkages of N-acetyl-neuraminic acid in which it is bound to galactose and N-acetyl-glucosamine are α-2,3- and α-2,6-ketosidic bonds. This terminally exposed position allows sialoconjugates to be recognized by receptors of cells, viruses and bacteria, thus to be involved in a wide variety of biological processes.

The pentasaccharide 6'''-O-sialyl-LNT (LST b, Galβ(1-3)-[Neu5Acα(2-6)-]GlcNAcβ(1-3)-Galβ(1-4)-Glc) is a human milk oligosaccharide and represents a common structural element in some other sialylated human milk oligosaccharides (Urashima et al.: Milk Oligosaccharides, Nova Medical Books, NY, 2011); they are listed in Table 1.

TABLE 1

Selected sialylated HMOs

| No | HMO name | HMO structure |
|---|---|---|
| 1 | LST b | Galβ(1-3)-[Neu5Acα(2-6)-]GlcNAcβ(1-3)-Galβ(1-4)-Glc |
| 2 | F-LST b | Fucα(1-2)-Galβ(1-3)-[Neu5Acα(2-6)-]GlcNAcβ(1-3)-Galβ(1-4)-Glc |
| 3 | DS-LNT | Neu5Acα(2-3)-Galβ(1-3)-[Neu5Acα(2-6)-]GlcNAcβ(1-3)-Galβ(1-4)-Glc |
| 4 | FDS-LNT I | Neu5Acα(2-3)-Galβ(1-3)-[Neu5Acα(2-6)-]{Fucα(1-4)-}GlcNAcβ(1-3)-Galβ(1-4)-Glc |
| 5 | FDS-LNT II | Neu5Acα(2-3)-Galβ(1-3)-[Neu5Acα(2-6)-]GlcNAcβ(1-3)-Galβ(1-4)-[Fucα(1-3)-]Glc |
| 6 | FS-LNH I | Neu5Acα(2-3)-Galβ(1-3)-[Neu5Acα(2-6)-]GlcNAcβ(1-3)-[Galβ(1-4)-{Fucα(1-3)-}GlcNAcβ(1-6)-]Galβ(1-4)-Glc |

TABLE 1-continued

Selected sialylated HMOs

| No | HMO name | HMO structure |
|---|---|---|
| 7 | DS-LNH II | Neu5Acα(2-3)-Galβ(1-3)-[Neu5Acα(2-6)-]GlcNAcβ(1-3)-[Galβ(1-4)-GlcNAcβ(1-6)-]Galβ(1-4)-Glc |
| 8 | FDS-LNH I | Neu5Acα(2-3)-Galβ(1-3)-[Neu5Acα(2-6)-]GlcNAcβ(1-3)-[Fucα(1-2)-Galβ(1-4)-GlcNAcβ(1-6)-]Galβ(1-4)-Glc |
| 9 | FDS-LNH II | Neu5Acα(2-3)-Galβ(1-3)-[Neu5Acα(2-6)-]GlcNAcβ(1-3)-[Galβ(1-4)-{Fucα(1-3)-}GlcNAcβ(1-6)-]Galβ(1-4)-Glc |
| 10 | TS-LNH | Neu5Acα(2-3)-Galβ(1-3)-[Neu5Acα(2-6)-]GlcNAcβ(1-3)-[Neu5Acα(2-6)-Galβ(1-4)-GlcNAcβ(1-6)-]Galβ(1-4)-Glc |

DS-LNT has recently been found to be preventive against necrotising enterocolitis (NEC) in rat model (Jantscher-Krenn et al. Gut 61, 1417 (2012), WO 2012/106665).

More thorough research studies of cell-cell interactions, mechanism of cancer malignancy and/or determination of the bioactive conformation of compounds that are involved in protein-glycan recognition processes have required greater quantities of such oligosaccharides, but present enzymatic and/or microbial methods have not been able to provide with them in sufficient amounts and/or purities. Synthetic chemical methods, adapted to provide them in sufficient purity, have required many expensive reaction steps and the extensive use of protection-deprotection sequences during the synthesis, and afford compounds only in mg quantities, as demonstrated by the synthesis of an α(2-3)/α(2-6)-disialyl lactotetraosyl ceramide and a disialyl Lewis A ganglioside (Ando et al. J. Carbohydr. Chem. 20, 425 (2001), Carbohydr. Res. 338, 503 (2003)).

There has been a need, therefore, for an efficient method of making a diverse group of sialylated and/or fucosylated LNT derivatives and their analogs. There has been a particular need for a method that can be readily scaled-up for potential industrial use.

SUMMARY OF THE INVENTION

The invention relates to a method for making a 3-O-galactosyl-GlcNAc or -GalNAc derivative of formula 1 and salts thereof

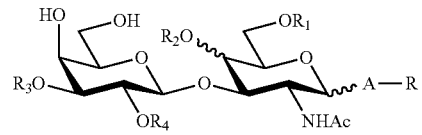

wherein R is selected from —OH, —N$_3$ and —OR$_6$
wherein R$_6$ is selected from allyl optionally substituted by one or more methyl, propargyl optionally substituted by one or more methyl, 2-trimethylsilyl-ethyl, —(CH$_2$)$_n$—NH$_2$ and —(CH$_2$)$_n$—N$_3$ wherein integer n is 1 to 10, preferably 2 or 3,
R$_1$ is selected from sialyl moiety, —SO$_3$H and —CH(R$_5$)—COOH wherein R$_5$ is selected from H, alkyl and benzyl,
R$_2$ is selected from H and fucosyl moiety,
R$_3$ is selected from H and sialyl moiety, $R_4$ is selected from H and fucosyl moiety, provided that at least one of $R_3$ and $R_4$ is H, and A is a divalent carbohydrate linker, comprising the steps:

a) sialylation, sulfation or carboxymethylation of a compound of formula 2

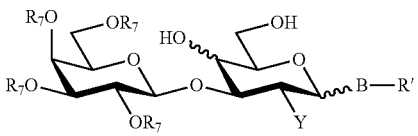

2 wherein R' is selected from —$N_3$ and —$OR'_6$ wherein $R'_6$ is selected from allyl optionally substituted by one or more methyl, propargyl optionally substituted by one or more methyl, a group removable by hydrogenolysis, 2-trimethylsilyl-ethyl and —$(CH_2)_n$—$N_3$ wherein integer n is 1 to 10, preferably 2 or 3, $R_7$ is independently acyl, Y is selected from —NHAc, haloalkanoylamido, —$NAc_2$, haloalkoxycarbonylamino, 2,3-diphenylmaleimido, 2,3-dimethylmaleimido and —$N_3$, and B is a divalent carbohydrate linker in protected form, b) optional fucosylation of the compound obtained in step a), c) de-O-acylation and/or basic hydrolysis, optional mild acidic hydrolysis and optional transformation of Y to —NHAc of the compound obtained in step a) or step b), d) optional sialylation or fucosylation of the compound obtained in step c), and e) optional catalytic hydrogenolysis and/or anomeric deprotection of the compound obtained in step d).

Furthermore the invention provides compounds of formula 11 and salts thereof

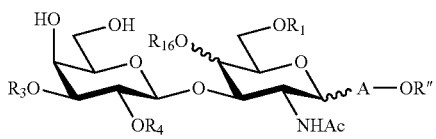

11 wherein R" is a group removable by hydrogenolysis,

A is a divalent carbohydrate linker, $R_1$ is selected from sialyl moiety, —$SO_3H$ and —$CH(R_5)$—COOH wherein $R_5$ is selected from H, alkyl and benzyl, $R_3$ is selected from H and sialyl moiety, $R_4$ is selected from H and fucosyl moiety, provided that at least one of $R_3$ and $R_4$ is H, and $R_{16}$ is selected from H and moiety C, preferably H,

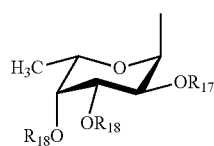

C wherein $R_{17}$ and $R_{18}$, independently, are selected from H and a group removable by hydrogenolysis, and compounds of formula 12

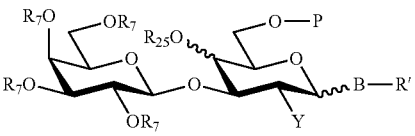

12 wherein R' is selected from —$N_3$ and —$OR'_6$ wherein $R'_6$ is selected from allyl optionally substituted by one or more methyl, propargyl optionally substituted by one or more methyl, a group removable by hydrogenolysis, 2-trimethylsilyl-ethyl and —$(CH_2)_n$—$N_3$ wherein integer n is 1 to 10, preferably 2 or 3, $R_7$ is independently acyl, Y is selected from —NHAc, haloalkanoylamido, —$NAc_2$, haloalkoxycarbonylamino, 2,3-diphenylmaleimido, 2,3-dimethylmaleimido and —$N_3$, and B is a divalent lactosyl linker in protected form, P is selected from protected sialyl moiety, —$SO_3H$ and —$CH(R_5)$—$COOR_{10}$ wherein $R_5$ is selected from H, alkyl and benzyl, $R_{10}$ is selected from alkyl and benzyl, and $R_{25}$ is selected from moiety I and H, preferably H,

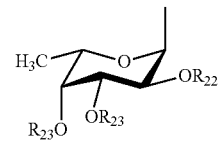

I wherein $R_{22}$ and $R_{23}$ are, independently, selected from a group removable by hydrogenolysis and acyl.

DETAILED DESCRIPTION OF THE INVENTION

In accordance with this invention, the term "acyl" preferably means an R*—C(=O)— group, wherein R* can be H, linear or branched alkyl with 1-6 carbon atoms or aryl including phenyl and naphthyl, preferably phenyl, such as formyl, acetyl, propionyl, butyryl, pivaloyl, benzoyl, etc. The alkyl and aryl residues can be unsubstituted or substituted one or several times, preferably 1-5 times, more preferably 1-3 times. The substituents can preferably be alkyl (for aromatic acyl), hydroxy, alkoxy, carboxy, oxo (for alkyl, forming a keto or aldehyde function), alkoxycarbonyl, alkylcarbonyl, formyl, aryl, aryloxycarbonyl, aryloxy, arylamino, arylcarbonyl, amino, mono- and dialkylamino, carbamoyl, mono- and dialkyl-aminocarbonyl, alkylcarbonylamino, cyano, alkanoyloxy, nitro, alkylthio and/or halogen (F, Cl, Br, I). The substituents on aryl and alkyl moieties of acyl groups can modify the general chemical characteristics of the acyl group, and thereby the characteristics, such as stability, solubility and the ability to form crystals, of a molecule as a whole.

Herein, the term "group removable by hydrogenolysis" preferably means a protecting group whose C—O bond can be cleaved by hydrogen in the presence of a catalytic amount of palladium, Raney nickel or any other conventional hydrogenolysis catalyst to regenerate the protected —OH group. Such protecting groups are described in Wuts and Greene: *Protective Groups in Organic Synthesis*, John Wiley & Sons, 2007, and include benzyl, diphenylmethyl (benzhydryl), 1-naphthylmethyl, 2-naphthylmethyl and triphenylmethyl (trityl) groups, each of which can be optionally substituted by one or more of the following groups: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). A preferred protecting group is benzyl optionally substituted with one or more of the following groups: phenyl, alkyl and halogen, particularly unsubstituted benzyl, 4-chlorobenzyl, 3-phenylbenzyl and 4-methylbenzyl groups. These preferred and particularly preferred protecting groups have the advantage that the by-products of their hydrogenolysis are exclusively toluene or substituted toluene. Such by-products can easily be removed, even in multi-ton quantities, from water-soluble oligosaccharide products via evaporation and/or extraction processes.

Also herein, the term "α-sialyl" or "sialyl" preferably means—in accordance with Chen and Varki *ACS Chem. Biol.* 5, 163 (2010)—a glycosyl moiety of any naturally occurring or modified neuraminic acid or sialic acid derivative or an analogue thereof having an α-glycosidic linkage. Preferred neuraminic acid derivatives are N-acetyl-(Neu5Ac), N-glycolyl-(Neu5Gc) and deamino-neuraminic acid (3-deoxy-D-glycero-D-galacto-nonulosonic acid, KDN), as well as Neu5Ac, Neu5Gc and KDN derivatives that are derivatized with linkers, reactive functional groups, detectable labels or targeting moieties, and/or substituted at C-4, C-7-, C-8 and/or C-9, especially at C-9, with acyloxy, alkoxy, halogen or azido. The preferred sialyl moiety is the glycosyl residue of Neu5Ac (see Scheme 1). It should be noted that the term "sialyl" in the generally accepted trivial names of human milk oligosaccharides and Lewis type oligosaccharides always refers to Neu5Ac.

Scheme 1

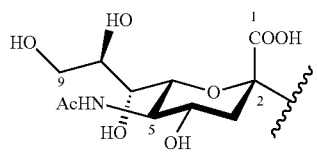

Further herein, the term "fucosyl" preferably means a L-fucopyranosyl group (see Scheme 2) attached to a core oligosaccharide with α-interglycosidic linkage.

Scheme 2

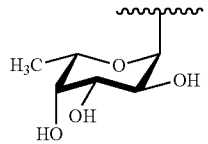

Still further herein, the term "salt" in connection with sialylated, sulfated and carboxymethylated compounds described in the application preferably means an associated ion pair consisting of the negatively charged acid residue and one or more cations in any stoichiometric proportion. Cations, which are atoms or molecules with a positive charge, can be inorganic or organic. Preferred inorganic cations are ammonium ion, alkali metal, alkali earth metal and transition metal ions, more preferably $Na^+$, $K^+$, $Ca^{2+}$, $Mg^{2+}$, $Ba^{2+}$, $Fe^{2+}$, $Zn^{2+}$, $Mn^{2+}$ and $Cu^{2+}$, more preferably $K^+$, $Ca^{2+}$, $Mg^{2+}$, $Ba^{2+}$, $Fe^{2+}$ and $Zn^{2+}$. Preferred basic organic compounds in positively charged form are diethyl amine, triethyl amine, diisopropyl ethyl amine, ethanolamine, diethanolamine, triethanolamine, imidazole, piperidine, piperazine, morpholine, benzyl amine, ethylene diamine, meglumin, pyrrolidine, choline, tris-(hydroxymethyl)-methyl amine, N-(2-hydroxyethyl)-pyrrolidine, N-(2-hydroxyethyl)-piperidine, N-(2-hydroxyethyl)-piperazine, N-(2-hydroxyethyl)-morpholine, L-arginine, L-lysine, oligopeptides having L-arginine or L-lysine unit or oligopeptides having free amino group on N-terminal, etc., all in protonated form. Such salts can be used in a conventional manner to modify the characteristics of the compounds of this invention, such as their stability, compatibility to excipients, solubility and ability to form crystals.

Yet further herein, the term "alkyl" preferably means a linear or branched hydrocarbon group with 1-6 carbon atoms, such as methyl, ethyl, n-propyl, i-propyl, n-butyl, i-butyl, s-butyl, t-butyl, etc.; the term "haloalkanoylamido" preferably means a halogen substituted $C_1$-$C_6$-alkanoylamido such as chloroacetamido, trichloroacetamido, trifluoroacetamido, etc.; the term "haloalkoxycarbonylamino" preferably means a $C_1$-$C_6$-alkyloxycarbonyl-NH— group substituted by one or more halogen atoms such as 2,2,2-trichloroethoxycarbonylamino, etc.; the term "optionally substituted phenyl" and "optionally substituted benzyl" preferably mean a phenyl or benzyl group, respectively, that is not substituted or substituted by 1 to 5, preferably 1 to 3, more preferably 1 or 2 substituents selected from the group consisting of alkyl, halogen, alkoxy, phenyl, nitro, haloalkyl, haloalkoxy, amino, alkylamino, dialkylamino, acylamino, carbamoyl, N-alkylcarbamoyl and N,N-dialkyl carbamoyl; the term "cycloalkylidene" preferably means a $C_3$-$C_8$-cycloalkylidene group optionally substituted with alkyl(s) wherein the cycloalkyl group with the optional substituent(s) is of 3-8 carbon atoms, such as cyclopropyl, cyclopentyl, cyclohexyl, cycloheptyl or 4,4-dimethyl-cyclohexyl.

The present invention provides an efficient approach to a diverse group of sialylated and optionally fucosylated 3'-O-galactosyl-6-O-sialyl-GlcNAc or -GalNAc derivatives and analogs thereof based on the unique combination of chemical and enzymatic glycosylation steps. The claimed method is attractive for scale-up developments and therefore may imply a potential industrial process.

The first aspect of the invention relates to a method for making a 3-O-galactosyl-GlcNAc or -GalNAc derivative of formula 1 and salts thereof

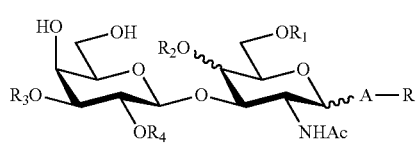

wherein R is selected from —OH, —$N_3$ and —$OR_6$
wherein $R_6$ is selected from allyl optionally substituted by one or more methyl, propargyl optionally substituted by one or more methyl, 2-trimethylsilyl-ethyl, —$(CH_2)_n$—$NH_2$ and —$(CH_2)_n$—$N_3$ wherein integer n is 1 to 10, preferably 2 or 3, $R_1$ is selected from sialyl moiety, —$SO_3H$ and —$CH(R_5)$—COOH wherein $R_5$ is selected from H, alkyl and benzyl, $R_2$ is selected from H and fucosyl moiety, $R_3$ is selected from H and sialyl moiety, $R_4$ is selected from H and fucosyl moiety, provided that at least one of $R_3$ and $R_4$ is H, and A is a divalent carbohydrate linker, comprising the steps:

a) sialylation, sulfation or carboxymethylation of a compound of formula 2

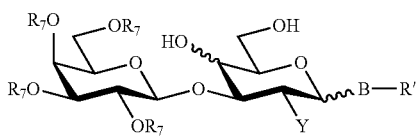

2 wherein R' is selected from —$N_3$ and —$OR'_6$ wherein $R'_6$ is selected from allyl optionally substituted by one or more methyl, propargyl optionally substituted by one or more methyl, a group removable by hydrogenolysis, 2-trimethylsilyl-ethyl and —$(CH_2)_n$—$N_3$ wherein integer n is 1 to 10, preferably 2 or 3, $R_7$ is independently acyl, Y is selected from —NHAc, haloalkanoylamido, —$NAc_2$, haloalkoxycarbonylamino, 2,3-diphenylmaleimido, 2,3-dimethylmaleimido and —$N_3$, and B is a divalent carbohydrate linker in protected form, b) optional fucosylation of the compound obtained in step a), c) de-O-acylation and/or basic hydrolysis, optional mild acidic hydrolysis and optional transformation of Y to —NHAc of the compound obtained in step a) or step b), d) optional sialylation or fucosylation of the compound obtained in step c), and e) optional catalytic hydrogenolysis and/or anomeric deprotection of the compound obtained in step d).

In step a) a compound according to formula 2 is employed in a sialylation or sulfation reaction, or a compound of formula 2 is carboxymethylated. In a compound of formula 2, B is a divalent carbohydrate linker in protected form. In this invention, the term "carbohydrate linker in protected form" preferably means any mono-, di- or oligosaccharide glycosyl residue which is attached to the R' group by the C-1 (aldoses) or C-2 (ketoses) anomeric carbon, and at the same time it is also attached, via one of its non-glycosidic OH— groups, to the galactosylated aminodeoxy-hexose residue of the compound of formula 2. If this divalent glycosyl residue B differs from a monosaccharide, it may represent a linear or branched structure consisting of monosaccharide units that are linked to each other by interglycosidic linkages. The monosaccharide unit(s) of the divalent glycosyl residue B can be selected from any 5-9 carbon atom containing sugars consisting of aldoses (e.g. D-glucose, D-galactose, D-mannose, D-ribose, D-arabinose, L-arabinose, D-xylose, etc.), ketoses (e.g. D-fructose, D-sorbose, D-tagatose, etc.), deoxysugars (e.g. L-rhamnose, L-fucose, etc.), deoxyaminosugars (e.g. N-acetylglucosamine, N-acetylmannosamine, N-acetylgalactosamine, etc.), uronic acids, ketoaldonic acids (e.g. sialic acid) and like. Preferably, the divalent glycosyl moiety B is a lactosyl moiety or an oligosaccharide moiety that consists of a lactosyl moiety and at least one monosaccharide unit selected from the group consisting of galactose, N-acetylglucosamine, fucose and N-acetyl neuraminic acid. The divalent lactosyl moiety is attached to the R' group by its C-1 anomeric carbon atom, and at the same time it is also attached, via one of its non-glycosidic OH— groups, preferably via its 3'-OH group to the galactosylated aminodeoxy-hexose residue of the compound of formula 2. The divalent lactosyl moiety defined above can be optionally substituted by other glycosyl residues, preferably on its 3-OH group by a fucosyl moiety, or on its 6'-OH group by a N-acetyllactosaminyl moiety, which N-acetyllactosaminyl moiety can optionally be further substituted by an N-acetyl neuraminyl moiety on its 6-OH, or by a fucosyl on its 3-OH or 2'-OH. These oligosaccharide substructures can be found in human milk oligosaccharides. The functional groups of the divalent glycosyl residue B are protected, preferably the free OH groups are acylated (e.g acetylated, benzoylated) and the carboxy group of the optional N-acetyl neuraminyl moiety is blocked in ester form (e.g. methyl, ethyl or benzyl ester). The axial OH— group of any galactose in moiety B is optionally protected.

In a preferred embodiment of the compounds of formula 2, the R' group has β-orientation. Also preferably, the moiety B is attached to the parent carbohydrate backbone by β-linkage. Compounds of formula 2 wherein B is a divalent carbohydrate linker in protected form can be synthesized by using multistep chemical glycosylation procedures as described in or by analogy to e.g. Xia et al. *Bioorg. Med. Chem. Lett.* 9, 2941 (1999), Pozsgay et al. *Tetrahedron* 48, 10249 (1992), Aly et al. *Carbohydr. Res.* 316, 121 (1999) and WO 2012/155916.

In carrying out step a) the primary free OH group of a compound of formula 2 is regioselectively sialylated, sulfated or carboxymethylated, without affecting the neighbouring secondary OH— group, to give a compound of formula 4

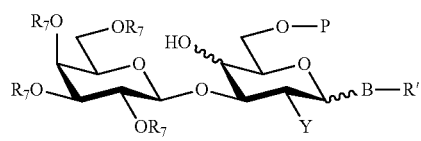

4 wherein R', $R_7$, B and Y are as defined above, and

P is selected from a protected sialyl moiety, —$SO_3H$ and —$CH(R_5)$—$COOR_{10}$ wherein $R_5$ is selected from H, alkyl and benzyl, $R_{10}$ is selected from alkyl and benzyl.

For the chemical sialylation, suitably protected and activated sialyl donors are used. For the functional group protection of the sialyl donor, an array of protecting groups, mainly esters, ethers and acetals, are available to the skilled person. Among OH-protection possibilities, optionally substituted acyls, such as acetyl, benzoyl, chloroacetyl or chlorobenzoyl, and ether-type groups such as benzyl are of synthetic usefulness; the carboxyl group can be protected by an ester, typically by a methyl, ethyl or benzyl ester; and the amino function can be masked by diacetyl, trifluoroacetyl, trichloroacetyl, Troc or Fmoc group, or as a cyclic carbamate with the adjacent 4-OH. The anomeric centre activation can be varied among halo, alkyl- or arylthio, dialkyl, dibenzyl or diaryl phosphite, or trihaloacetimidate, each of which is commonly used in sialoglycosidation methods. The protective group introduction and anomeric centre activations mentioned above can be carried out by known processes (see e.g. Ress et al. *Curr. Org. Synth.* 1, 31 (2004), Chen et al. *ACS Chem. Biol.* 5, 163 (2010) and references cited therein). The preferred sialyl donors are those disclosed in WO 2011/100979 and WO 2012/113404, among which the N-acetyl neuraminyl phosphite donors of formula 3

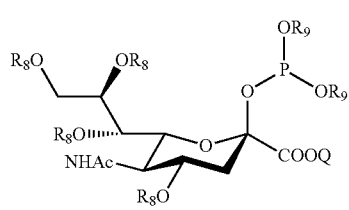

3 wherein $R_8$ is acyl, preferably acetyl,

Q is selected from alkyl and benzyl, preferably methyl, ethyl and benzyl, and $R_9$ is optionally substituted phenyl or benzyl, are especially preferred. The coupling reaction runs in aprotic solvent, preferably in dichloromethane, THF, methyl-THF, toluene, acetonitrile or in mixtures thereof, at temperatures between −78-0° C., in the presence of promoter like NBS, NIS, TMSOTf, TfOH, Tf$_2$O, ZnCl$_2$, BF$_3$OEt$_2$, LiClO$_4$, DTBPI, Bu$_4$NI, AgClO$_4$, LiClO$_4$, Sn(OTf)$_2$, iodine, montmorillonite, Tf$_2$NH or mixtures thereof, preferably TMSOTf. The sialylated product can be characterized by the following formula 4A

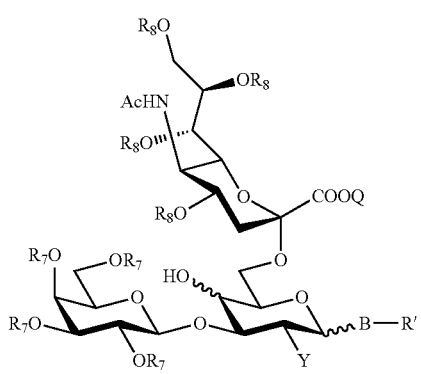

4A wherein R', $R_7$, $R_8$, B, Q and Y are as defined above.

If step a) is a sulfation step, a compound of formula 2 defined above is treated with SO$_3$-pyridine complex in a non-protic solvent to form a compound of formula 4B or a salt thereof

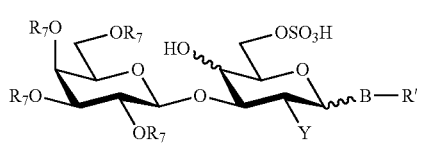

4B wherein R', $R_7$, B and Y are as defined above.

Also in step a), a compound of formula 2 can be carboxymethylated to give rise to a compound of formula 4C

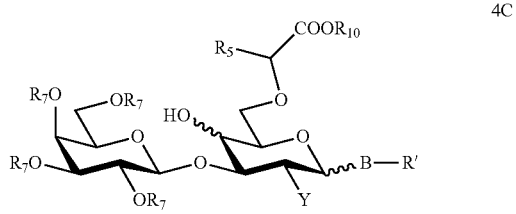

4C wherein $R_5$ is selected from H, alkyl and benzyl, $R_{10}$ is selected from alkyl and benzyl, and R', $R_7$, B and Y are as defined above.

The reaction can be carried out by the analogous process disclosed by Schwardt et al. *J. Med. Chem.* 52, 989 (2009). Thus the dihydroxy derivative of formula 2 is reacted with dibutyltin oxide to form a stannylidene acetal which reacts in a nucleophilic substitution reaction with the acetic acid derivative of formula L-CH($R_5$)—COOR$_{10}$ wherein L is a good leaving group such as halogen or sulfonate ester (e.g. mesyloxy, tosyloxy, trifluoromethanesulfonyloxy, etc.), and $R_5$ and $R_{10}$ are as defined above. In the reaction only the primary OH— group is alkylated, and, if the reagent acetic acid derivative is chiral, the substitution takes place with the inversion of configuration.

In step b), the sialylated, sulfated or carboxymethylated compound obtained in step a) is optionally fucosylated with a suitably protected and activated fucosyl donor. The fucosyl moiety is introduced at the remaining free secondary OH— group (4-OH) of the compound of formula 4. Thus, a fucosyl donor of formula 5

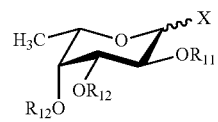

5 wherein X is selected from a halogen, —OC(=NH)CCl$_3$, —O-pentenyl, —OAc, —OBz and —SR$_{13}$, in which $R_{13}$ is alkyl or optionally substituted phenyl, $R_{11}$ is selected from acyl and a group removable by hydrogenolysis, and $R_{12}$ is selected from a group removable by hydrogenolysis, acyl or two $R_{12}$ groups together form a moiety

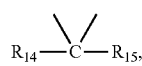

wherein $R_{14}$ and $R_{15}$ independently are alkyl or phenyl, or wherein $R_{14}$ and $R_{15}$ together with the carbon atom, to which they are attached, form cycloalkylidene, can be used in this reaction to give a compound of formula 6

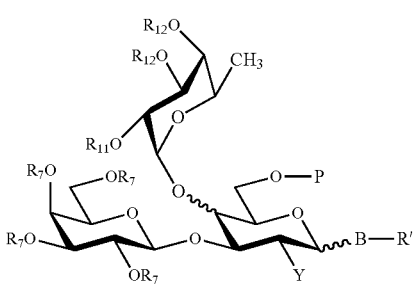

wherein R', $R_7$, $R_{11}$, $R_{12}$, B, P and Y are as defined above.

The fucosylation can be carried out in a conventional manner in an aprotic solvent or in a mixture of aprotic solvents in the presence of an activator, see Demchenko (Ed.): Handbook of Chemical Glycosylation Wiley (2008). The fucosylation reaction is generally promoted by heavy metal ions, mainly mercury or silver, and Lewis acids such as trimethylsilyl triflate or $BF_3$-etherate.

Preferably, a fucosyl halide (i.e., X is F, Cl, Br or I) is used because of its easy accessibility and satisfactory reactivity. Typically, anomeric halides follow the reactivity order F<Cl<Br<I for nucleophilic displacement. Glycosyl fluorides can be prepared by treating the appropriate precursors such as hemiacetals, glycosyl halides, glycosyl esters and S-glycosides with fluorinating reagents such as HF, AgF, $AgBF_4$, tetrabutyl ammonium fluoride, diethylaminosulfur trifluoride, 2-fluoro-1-methylpyridinium tosylate, Selectfluor, Deoxo-Fluor or 4-methyl(difluoroiodo)-benzene.

A fucosyl trichloroacetimidate (i.e., X is —OC(=NH)$CCl_3$) can be prepared by adding a sugar with a free anomeric OH to trichloroacetonitrile under inorganic or organic base catalysis. The resulting glycosyl donor can be activated by a catalytic amount of a Lewis acid, such as trimethylsilyl triflate or $BF_3$-etherate, for the glycosylation reaction.

Fucosyl acetates or benzoates (i.e., X is —OAc or —OBz) are preferably first subjected to electrophilic activation to provide a reactive intermediate and then treated with a nucleophilic OH-acceptor.

Typical activators of choice are Bronsted acids (e.g., p-TsOH, $HClO_4$ or sulfamic acid), Lewis acids (e.g., $ZnCl_2$, $SnCl_4$, triflate salts, $BF_3$-etherate, trityl perchlorate, $AlCl_3$ or triflic anhydride) or a mixture thereof.

Pentenyl fucosides (i.e., X is —O—$(CH_2)_3$—CH=$CH_2$) can be transglycosylated with appropriate glycosyl acceptors in the presence of a promoter such as NBS and NIS. Protic or Lewis acids (triflic acid, Ag-triflate, etc.) can enhance the reaction. The pentenyl glycosides can be prepared with the aid of n-pentenol by standard Fischer glycosylation of hemiacetals under acidic condition, by silver(I) salt promoted coupling of glycosyl bromides (Koenigs-Knorr method), or by glycosylation of 1-acetyl glycosides in the presence of tin(IV) chloride.

Thiofucosides (i.e., X is alkylthio- or optionally substituted phenylthio-group) can be activated by thiophilic promoters such as mercury(II) salts, $Br_2$, $I_2$, NBS, NIS, triflic acid, triflate salts, $BF_3$-etherate, trimethylsilyl triflate, dimethyl-methylthio sulphonium triflate, phenylselenyl triflate, iodonium dicollidine perchlorate, tetrabutylammonium iodide or mixtures thereof, preferably by $Br_2$, NBS, NIS or triflic acid.

Aprotic solvents such as toluene, THF, methyl-THF, DCM, chloroform, dioxane, acetonitrile, chlorobenzene, ethylene dichloride, DMSO, DMF or N-methylpyrrolidone or mixtures thereof, preferably DMF, toluene, DCM or mixtures thereof, more preferably toluene or DMF-DCM mixture can be used in this glycosylation reaction at −20 to 20° C., preferably at −10 to 5° C., with reaction time of 5 min to 2 hours. For thiophilic activation, $Br_2$, NBS or NIS can be used, optionally in the presence of triflic acid or a triflate derivative. Usually a slight excess of donor (1.1-1.2 eq.) is used compared to the acceptor. For quenching the reaction, water or a $C_1$-$C_6$ alcohol is generally used, preferably an aqueous or alcoholic solution of a base such as sodium carbonate, sodium bicarbonate, ammonia or triethyl amine, more preferably an aqueous $Na_2S_2O_3$/$NaHCO_3$ solution.

More preferably, the fucosyl donor is a compound of formula 5 wherein $R_{11}$ is as defined above, $R_{12}$ is acyl or a group removable by hydrogenolysis, and X is phenylthio optionally substituted with one or more alkyl. More preferably $R_{11}$ is benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl or 2,3,4,5,6-pentamethylbenzyl, $R_{12}$ is benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl, 2,3,4,5,6-pentamethylbenzyl or benzoyl optionally substituted by one or more halogens and X is unsubstituted phenylthio. Even more preferably, $R_{11}$ is benzyl or 4-methylbenzyl and $R_{12}$ is benzoyl or 4-chlorobenzoyl.

According to a preferred embodiment of step b), a compound of formula 4A, 4B or 4C defined above is reacted with a fucosyl donor of formula 5 giving rise to a compound of formula 6A, 6B or 6C, respectively, and salts thereof

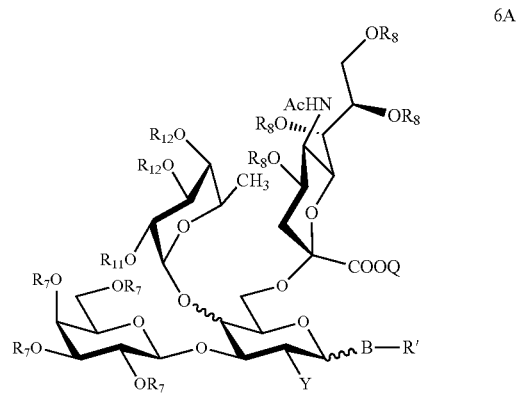

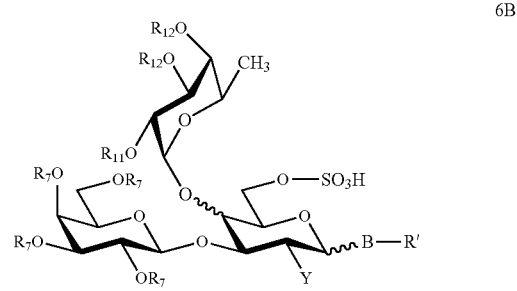

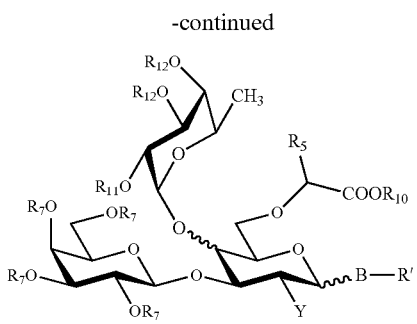

wherein R', $R_5$, $R_7$, $R_8$, $R_{10}$, $R_{11}$, $R_{12}$, B, Q and Y are as defined above.

In step c), the protecting groups of a compound obtained in step a) or step b) are removed except for the anomeric protection R', and optionally Y is converted into a —NHAc group.

Most of the protecting groups are O-acyls ($R_7$, $R_8$, the OH-protections in moiety B, and optionally $R_{11}$ and $R_{12}$). Acyl protective groups can be removed by a conventional base catalysed transesterification deprotection reaction wherein the acyl groups are removed in an alcohol solvent such as methanol, ethanol, propanol or t-butanol in the presence of an alcoholate such as NaOMe, NaOEt or KO$^t$Bu at 20-100° C. The alcohol solvent and the alcoholate should be matched. A co-solvent such as toluene or xylene can be beneficial in order to control particle size of the product and to avoid gel formation. Preferably, a catalytic amount of NaOMe is used in methanol (Zemplén de-O-acylation). Under this condition only O-acyls can be deprotected. If Y is —NAc$_2$, one of the acetyl groups can also be removed to make the Y group —NHAc. When Y is: haloalkanoylamido, haloalkoxycarbonylamino, 2,3-diphenylmaleimido, 2,3-dimethylmaleimido or —N$_3$, and ester groups (see group —COOQ or —COOR$_{10}$) remain intact under these conditions.

Acyloxy groups to OH, esters to carboxyl (see group —COOQ or —COOR$_{10}$) and the following Y— groups: haloalkanoylamido, halocarboxylamino, 2,3-diphenylmaleimido and 2,3-dimethylmaleimido to —NH$_2$ can be deprotected by basic hydrolysis, which is a base catalysed hydrolysis in water, alcohol or water-organic solvent mixtures, in homogeneous or heterogeneous reaction conditions at 0-100° C. Preferably, a strong base, such as LiOH, NaOH, KOH, Ba(OH)$_2$, K$_2$CO$_3$, a basic ion exchange resin or tetraalkylammonium hydroxides, is used, but the base can also be in an aqueous solution as well. If Y is —NAc$_2$, one of the acetyl groups can also be removed to make the Y group —NHAc. Preferably, the base is NaOH and the solvent is methanol. Azido Y group is not affected in this reaction.

Also in step c), a 2,2,2-trichloroethoxycarbonylamino Y— group can also be converted into free amino groups by means of Zn/HCl, and Y: —N$_3$ can be reduced to amino using e.g. PPh$_3$ or Cu/Zn (provided that R' is not azido or R'$_6$ is not —(CH$_2$)$_n$—N$_3$).

The free amino group obtained by one of the deprotective methods can then be acetylated without acetylating the free OH— groups. Selective N-acetylation in the presence of one or more hydroxyls can be carried out in a conventional manner with a slight excess of acetic anhydride or acetyl chloride (≈1.5-3 equiv.) at about 0-35° C. with or without added base. Any resulting overacetylated by-product(s) can be readily transformed into the desired compounds with e.g. NaOH/MeOH or NaOMe/MeOH treatment. Alternatively, the deprotected compound having a free amino group can be peracetylated (that is the amino group and all available OH groups are acetylated) followed by base catalysed transesterification (see above).

Also in step c), trichloroacetylamide Y— group can be transformed in one step to —NHAc with tributyltin hydride.

Also in step c), acetal/ketal group optionally present on the compounds of formulas 6A, 6B and 6C (i.e. when two $R_{12}$ groups together form a moiety

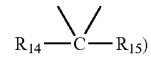

can be selectively deprotected by acid catalysed mild hydrolysis, i.e. by reacting the compounds with water or an alcohol in the presence of acid at pH>1-2 to produce OH— groups on the compounds. Acyl protective groups will not be affected because they can be deprotected only by extremely strong acidic hydrolysis (pH<1). Although the interglycosidic linkage and anomeric protecting groups of the compounds of formulas 6A, 6B and 6C can also be sensitive to acids, they can be split in the compounds of formulas 6A, 6B and 6C only by acidic hydrolysis at pH<1-2. The skilled person is able to distinguish which deprotective condition affects the acetal group while the acyl groups and the interglycosidic bonds remain intact. Water, which is a reagent, can also serve as solvent or co-solvent. Organic protic or aprotic solvents which are stable under acidic conditions and fully or partially miscible with water, such as $C_1$-$C_6$ alcohols, acetone, THF, dioxane, ethyl acetate or MeCN, can be also used in a mixture with water. The acid used is generally a protic acid, such as acetic acid, trifluoroacetic acid, HCl, formic acid, sulphuric acid, perchloric acid, oxalic acid, p-toluenesulfonic acid, benzenesulfonic acid or a cationic exchange resin, and can be present in from a catalytic amount to a large excess. The hydrolysis can be carried out at between 20° C. and reflux until completion of the reaction which can take from about 2 hours to 3 days depending on temperature, concentration and pH. Preferably, an organic acid, such as acetic acid, formic acid, chloroacetic acid or oxalic acid, is used. Preferably, a $C_1$-$C_6$ alcohol-acetonitrile or $C_1$-$C_6$ alcohol-water mixture is used in the presence of HCl or a sulfonic acid such as p-toluenesulfonic acid or camphorsulfonic acid. Alternatively, an anhydrous $C_1$-$C_6$ alcohol, such as methanol, ethanol, propanol and butanol, can be used for the cleavage of acetal via acid catalysed trans-acetalization/trans-ketalization processes. Catalytic amount of hydrogen chloride, sulphuric acid, perchloric acid, p-toluenesulfonic acid, acetic acid, oxalic acid, camphorsulfonic acid or a strong acidic ion-exchange resin can be used at temperatures of 20° C. to reflux.

Also in step c), any compound of formula 6A, 6B and 6C, wherein at least one of the $R_{11}$ and $R_{12}$ substituents is a group removable by hydrogenolysis, provided that R' is 2-trimethylsilylethyloxy and Y is not azido, can be subjected to catalytic hydrogenolysis in order to remove benzyl/substituted benzyl group(s). In addition, compounds of formula 6A, 6B and 6C, wherein at least one of the $R_{11}$ and $R_{12}$ substituents is a group removable by hydrogenolysis, provided that R'$_6$ is not a group removable by hydrogenolysis, can be treated with NaBrO$_3$ and Na$_2$S$_2$O$_4$ to remove the benzyl/substituted benzyl group(s) from the fucosyl residue.

The above mentioned deprotective steps can be carried out in any order. As a result, a compound of formula 7 and salts thereof can be obtained

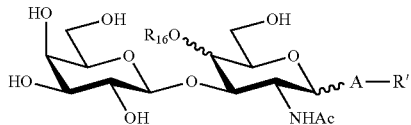

7 wherein R' is as defined above,
moiety A is a divalent carbohydrate linker,
$R_1$ is selected from sialyl, —$SO_3H$ and —$CH(R_5)$—COOH, wherein $R_5$ is as defined above, and
$R_{16}$ is selected from H and a moiety of formula C

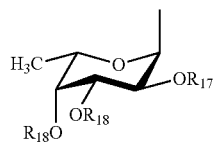

C wherein $R_{17}$ and $R_{18}$, independently, are selected from H and a group removable by hydrogenolysis.

The term "divalent carbohydrate linker" above preferably means any mono-, di- or oligosaccharide glycosyl residue which is attached to the R' group by the C-1 (aldoses) or C-2 (ketoses) anomeric carbon, and in the same time it is also attached, via one of its non-glycosidic OH— groups, to the galactosylated aminodeoxy-hexose residue of the compound of formula 7, as defined for moiety B above, in deprotected from, which means that the OH-protective groups and the ester protective group of the N-acetyl neuraminyl moiety (if present) in the divalent carbohydrate linker of moiety B are removed when carrying out step c), thus transforming moiety B into moiety A. Preferably, the divalent glycosyl moiety A is a lactosyl moiety or an oligosaccharide moiety that consists of a lactosyl moiety and at least one monosaccharide unit selected from the group consisting of galactose, N-acetylglucosamine, fucose and N-acetyl neuraminic acid. The divalent lactosyl moiety is attached to the R' group by its C-1 anomeric carbon atom, and in the same time it is also attached, via one of its non-glycosidic OH— groups, preferably via its 3'—OH group to the galactosylated aminodeoxy-hexose residue of the compound of formula 7. The divalent lactosyl moiety defined above can be optionally substituted by other glycosyl residues, preferably on its 3-OH group by a fucosyl moiety, or on its 6'—OH group by a N-acetyllactosaminyl moiety, which N-acetyllactosaminyl moiety can optionally be further substituted by an N-acetyl neuraminyl moiety on its 6-OH, or by a fucosyl on its 3-OH or 2'-OH.

In step d) a compound obtained in step c), that is a compound of formula 7 defined above, is optionally brought into a glycosidase mediated transsialylation or transfucosylation reaction and a compound of formula 10 and salts thereof can be obtained

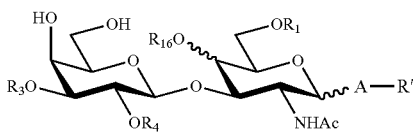

10 wherein R', $R_1$, $R_{16}$ and A are as defined above,
$R_3$ is selected from H and a sialyl, and
$R_4$ is selected from H and fucosyl moiety, provided that one but only of $R_3$ and $R_4$ is H.

With regard to the transsialylation reaction of step d), a compound of formula 7 is reacted with a sialyl donor, preferably a N-acetyl neuraminyl donor, under the catalysis of an enzyme having α2-3-transsialidase activity. Typical natural sialyl donors can be selected from, but are not limited to, 3'-O-sialyl-lactose, fetuin, gangliosides, O- or N-linked glycopeptides, all of which contain a sialic acid α-2,3-linked to a terminal β-galactoside residue, or polysialic acid with α-2,8-linkage. Also preferably, the sialyl donor used in step d) can be characterized by formula 8 and salts thereof,

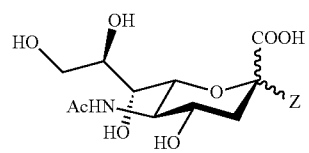

8 wherein Z is selected from the group consisting of azide, fluoro, optionally substituted phenoxy, optionally substituted pyridinyloxy, group D, group E, group F and group G

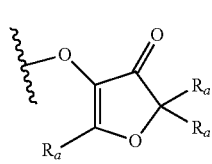

D

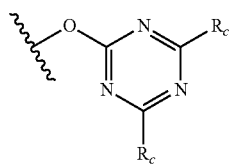

E

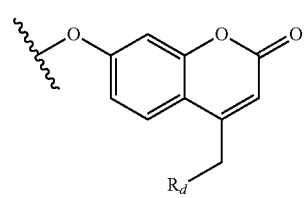

F

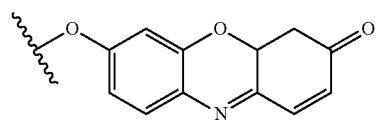

G wherein $R_a$ is independently H or alkyl, or two vicinal $R_a$ groups represent a=$C(R_b)_2$ group, wherein $R_b$ is independently H or alkyl, $R_c$ is independently selected from the group consisting of alkoxy, amino, alkylamino and dialkylamino, $R_d$ is selected from the group consisting of H, alkyl and —C(=O)$R_e$, wherein $R_e$ is OH, alkoxy, amino, alkylamino, dialkylamino, hydrazino, alkylhydrazino, dialkylhydrazino or trialkylhydrazino. Among the sialyl donors 4-methylumbelliferyl and optionally substituted phenyl N-acetyl-α-neuraminosides and 3'-O-sialyl-lactose, more commonly p-nitrophenyl N-acetyl-α-neuraminoside and 3'-O-sialyl-lactose, are of high preference.

Enzymes having α2-3-transsialidase activity are preferably selected from a sialidase or transsialidase as described in the following, e.g. from sialidases (EC 3.2.1.18) and transsialidases (EC 2.4.1.-) as classified according to the the GH33 family. They are retaining enzymes. Sialidases and trans-sialidases are widely distributed in nature. They are found particularly in diverse virus families and bacteria, and also in protozoa, some invertebrates and mammals. These enzymes differ in their biochemical properties, e.g., kinetics, binding affinity or substrate preference. Nevertheless, they possess conserved domains and structural similarities. Transsialidases differ from sialidases since they can transfer sialic acids, preferably α-2,3-bonded sialic acids, from a donor molecule to an acceptor derivative, which is preferably a terminal galactose moiety with a β-interglycosidic linkage. As a result of this transfer, an α-glycosidic bond is be formed between the sialic acid and the acceptor. However, if there is no suitable acceptor, the transsialidase hydrolyses the sialic acid.

The first transsialidase enzyme described was found in *Trypanosoma cruzi*, a protozoa which causes Chagas disease. This transsialidase (TcTS) has been extensively studied. Since that time transsialidases have been detected in several other trypanosome types such as *Trypanosoma brucei gambiense*, *Trypanosoma brucei rhodesiense*, *Trypanosoma brucei brucei* and *Trypanosoma congolense*. Moreover, the existence of transsialidases has been shown in *Endotrypanum* types, in *Corynebacterium diphtherias* and even in human plasma.

Sialidases can be classified into two different subgroups, endo- and exo-sialidases. The endo-sialidases hydrolyse sialic acid linkages internal to macromolecules, while the exo-sialidases attack terminal sialic acid linkages, and desialylate glycoproteins, glycopeptides, gangliosides, oligosaccharides and polysaccharides. Recently, sialidases from *Bifidobacterium bifidum* and *Bifidobacterium longum* subsp. *infantis* have been identified, cloned and characterized. These sialidases can cleave and so recognize both α-2,3- and α-2,6-linked sialosides. Sialidases from *Bifidobacterium longum* subsp. *infantis* have a consistent preference for α-2,6-linkage whereas sialidases from *Bifidobacterium bifidum* have a consistent preference for α-2,3-linkage. These enzymes are also capable of acting as catalysts for sialylation reactions due to their transsialidase activity and thus may be used in the context of the method of the present invention, preferably under kinetically controlled conditions.

Sialidases, which may be employed in the context of the present invention, may also comprise engineered sialidases. Based on sequence and structure comparisons, sialidase from *Trypanosoma rangeli* may be mutated at six positions, wherein the resulting mutant is able to display a significant level of transsialidase activity (see Paris et al. *J. Mol. Biol.* 345, 923 (2005)).

Even more preferably, the enzyme having a sialidase and/or transsialidase activity may be selected from sialidases or transsialidases derived from *Bifidobacterium longum* subsp. *infantis* ATCC 15697, *Bifidobacterium bifidum* JCM1254, *Bifidobacterium bifidum* S17, *Bifidobacterium bifidum* PRL2010, *Bifidobacterium bifidum* NCIMB 41171, *Trypanosoma cruzi*, etc.

Even more preferably enzyme having a sialidase and/or transsialidase activity may be selected from sialidases or transsialidases as defined according to the following deposit numbers: gi|213524659 (*Bifidobacterium longum* subsp. *infantis* ATCC 15697), gi|213523006 *Bifidobacterium longum* subsp. *infantis* ATCC 15697), siab2 (*Bifidobacterium bifidum* JCM1254), further sialidases or transsialidases from *Bifidobacterium bifidum* JCM1254, gi|309252191 (*Bifidobacterium bifidum* S17), gi|309252190 (*Bifidobacterium bifidum* S17), gi|310867437 (*Bifidobacterium bifidum* PRL2010), gi|310867438 (*Bifidobacterium bifidum* PRL2010), gi|224283484 (*Bifidobacterium bifidum* NCIMB 41171), gi|313140638 (*Bifidobacterium bifidum* NCIMB 41171), gi|47252690 (*Trypanosoma cruzi*), gi|432485 (*Trypanosoma cruzi*), gi|343957998 (*Trypanosoma congolense*), gi|343958004 (*Trypanosoma congolense*) etc., or a sequence exhibiting a sequence identity with the sequence of one of the above mentioned enzymes having a sialidase and/or transsialidase activity of at least 70%, more preferably at least 80%, equally more preferably at least 85%, even more preferably at least 90% and most preferably at least 95% or even 97%, 98% or 99% as compared to the entire wild type sequence on amino acid level.

Particularly preferred sialidases with sialidase/transsialidase activity are listed in the following Table 2:

TABLE 2

Preferred sialidases/transsialidases

| GI number in GenBank Database | Organisms |
| --- | --- |
| gi\|213524659 | *Bifidobacterium longum* subsp. *infantis* ATCC 15697 |
| gi\|213523006 | *Bifidobacterium longum* subsp. *infantis* ATCC 15697 |
| gi\|309252191 | *Bifidobacterium bifidum* S17 |
| gi\|309252190 | *Bifidobacterium bifidum* S17 |
| gi\|310867437 | *Bifidobacterium bifidum* PRL2010 |
| gi\|310867438 | *Bifidobacterium bifidum* PRL2010 |
| gi\|224283484 | *Bifidobacterium bifidum* NCIMB 41171 |
| gi\|313140638 | *Bifidobacterium bifidum* NCIMB 41171 |
| gi\|47252690 | *Trypanosoma cruzi* |
| gi\|432485 | *Trypanosoma cruzi* |
| gi\|343957998 | *Trypanosoma congolense* |
| gi\|343958004 | *Trypanosoma congolense* |

In the transsialylation reaction according to step d) a compound of formula 10A and salts thereof can be made

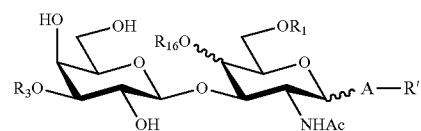

10A wherein R', $R_1$, $R_{16}$ and A are as defined above, and $R_3$ is a sialyl, preferably N-acetyl-neuraminyl moiety.

With regard to the transfucosylation reaction of step d), a compound of formula 7 is reacted with a fucosyl donor under the catalysis of an enzyme having α1-2-transfucosidase activity. Typical fucosyl donors can be selected from, but are not limited to, 2'-O-fucosyl-lactose, difucosyl-lactose, and fucose donors of formula 9

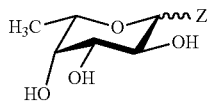

wherein Z is selected from the group consisting of azide, fluoro, optionally substituted phenoxy, optionally substituted pyridinyloxy, group D, group E, group F and group G

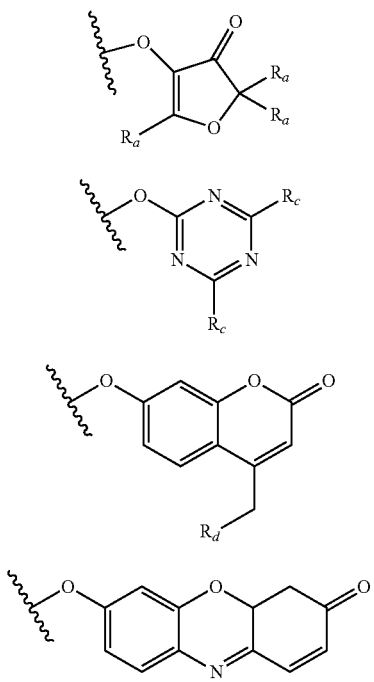

wherein $R_a$ is independently H or alkyl, or two vicinal $R_a$ groups represent a=$C(R_b)_2$ group, wherein $R_b$ is independently H or alkyl, $R_c$ is independently selected from the group consisting of alkoxy, amino, alkylamino and dialkylamino, $R_d$ is selected from the group consisting of H, alkyl and —C(=O)$R_e$, wherein $R_e$ is OH, alkoxy, amino, alkylamino, dialkylamino, hydrazino, alkylhydrazino, dialkylhydrazino or trialkylhydrazino.

The enzyme exhibiting α1-2-transfucosidase activity is preferably selected from fucosidases, transfucosidases and fucosynthases as classified according to EC 3.2.1.38 and 3.2.1.51. α-L-Fucosidases are widely spread in living organisms such as mammals, plants, fungi and bacteria. These enzymes belong to the families 29 and 95 of the glycoside hydrolases (GH29 and GH95) as defined by the CAZY nomenclature (http://www.cazy.org). Fucosidases from GH29 are retaining enzymes (3D structure: (β/α)$_8$) whereas fucosidases from GH95 are inverting enzymes (3D structure: (α/α)$_6$). The substrate specificity of the GH29 family is broad whereas that of the GH95 family is strict to α1,2-linked fucosyl residues. α-L-Fucosidases generally hydrolyse the terminal fucosyl residue from glycans. These enzymes are also capable of acting as catalysts for fucosylation reactions due to their transfucosylation activity and thus may be used in the context of the method of the present invention, preferably under kinetically controlled conditions.

Fucosidases, which may be employed in the context of the present invention, may also comprise engineered fucosidases. Such engineered fucosidases preferably comprise engineered α-L-fucosidases, preferably engineered fucosidases derived from fucosidases as described above, e.g. an engineered α-1,2-L-fucosynthase from *Bifidobacterium bifidum*, α-L-fucosynthases from *Sulfolobus solfataricus* and *Thermotoga maritime*, etc. Such engineered fucosidases show an acceptor dependent regioselectivity and are devoid of product hydrolysis activity. Furthermore, engineered fucosidases preferably comprise α-L-fucosidase from *Thermotoga maritima*, which has also been recently converted into an efficient α-L-transfucosidase by directed evolution (see Osanjo et al. *Biochemistry* 46, 1022 (2007)).

Even more preferably, the enzyme having a fucosidase and/or trans-fucosidase and/or fucosynthase activity may be selected from α-L-fucosidases derived from *Thermotoga maritima* MSB8, *Sulfolobus solfataricus* P2, *Bifidobacterium bifidum* JCM 1254, *Bifidobacterium bifidum* JCM 1254, *Bifidobacterium longum* subsp. *infantis* ATCC 15697, *Bifidobacterium longum* subsp. *infantis* ATCC 15697, *Bifidobacterium longum* subsp. *Infantis* JCM 1222, *Bifidobacterium bifidum* PRL2010, *Bifidobacterium bifidum* S17, *Bifidobacterium longum* subsp *longum* JDM 301, *Bifidobacterium dentium* Bd1, or *Lactobacillus casei* BL23, etc.

Even more preferably the enzyme having a fucosidase and/or trans-fucosidase and/or fucosynthase activity may be selected from following α-L-fucosidases as defined according to the following deposit numbers gi|4980806 (*Thermotoga maritima* MSB8), gi|13816464 (*Sulfolobus solfataricus* P2), gi|34451973 (*Bifidobacterium bifidum* JCM 1254), gi|242345155 (*Bifidobacterium bifidum*, JCM 1254), gi|213524647 (*Bifidobacterium longum* subsp. *infantis*, ATCC 15697), gi|213522629 (*Bifidobacterium longum* subsp. *infantis* ATCC 15697), gi|213522799 (*Bifidobacterium longum* subsp. *infantis* ATCC 15697), gi|213524646 (*Bifidobacterium longum* subsp. *infantis* ATCC 15697), gi|320457227 (*Bifidobacterium longum* subsp. *infantis* JCM 1222), gi|320457408 (*Bifidobacterium longum* subsp. *infantis* JCM 1222), gi|320459369 (*Bifidobacterium longum* subsp. *infantis* JCM 1222), gi|320459368 (*Bifidobacterium longum* subsp. *infantis* JCM 1222), gi|310867039 (*Bifidobacterium bifidum* PRL2010), gi|310865953 (*Bifidobacterium bifidum* PRL2010), gi|309250672 (*Bifidobacterium bifidum* S17), gi|309251774 (*Bifidobacterium bifidum* S17), gi|296182927 (*Bifidobacterium longum* subsp *longum* JDM 301), gi|296182928 (*Bifidobacterium longum* subsp *longum* JDM 301), gi|283103603 (*Bifidobacterium dentium* Bd1), gi|190713109 (*Lactobacillus casei* BL23), gi|190713871 (*Lactobacillus casei* BL23), gi|190713978 (*Lactobacillus casei* BL23), etc., or a sequence exhibiting a sequence identity with the sequences of one of the above mentioned enzymes having a fucosidase and/or trans-fucosidase activity of at least 70%, more preferably at least 80%, equally more preferably at least 85%, even more preferably at least 90% and most preferably at least 95% or even 97%, 98% or 99% as compared to the entire wild type sequence on amino acid level.

Particularly preferred α-L-fucosidases with fucosidase/trans-fucosidase/fucosynthase activity are listed in the following Table 3:

TABLE 3

Preferred α-L-fucosidases

| GI number in GenBank Database | Organisms |
|---|---|
| gi\|4980806 | *Thermotoga maritima* MSB8 |
| gi\|13816464 | *Sulfolobus solfataricus* P2 |
| gi\|34451973 | *Bifidobacterium bifidum* JCM 1254 |
| gi\|242345155 | *Bifidobacterium bifidum* JCM 1254 |
| gi\|213524647 | *Bifidobacterium longum* subsp. *infantis* ATCC 15697 |
| gi\|213522629 | *Bifidobacterium longum* subsp. *infantis* ATCC 15697 |
| gi\|213522799 | *Bifidobacterium longum* subsp. *infantis* ATCC 15697 |
| gi\|213524646 | *Bifidobacterium longum* subsp. *Infantis* ATCC 15697 |
| gi\|320457227 | *Bifidobacterium longum* subsp. *infantis* JCM 1222 |
| gi\|320457408 | *Bifidobacterium longum* subsp. *infantis* JCM 1222 |
| gi\|320459369 | *Bifidobacterium longum* subsp. *infantis* JCM 1222 |
| gi\|320459368 | *Bifidobacterium longum* subsp. *infantis* JCM 1222 |
| gi\|310867039 | *Bifidobacterium bifidum* PRL2010 |
| gi\|310865953 | *Bifidobacterium bifidum* PRL2010 |
| gi\|309250672 | *Bifidobacterium bifidum* S17 |
| gi\|309251774 | *Bifidobacterium bifidum* S17 |
| gi\|296182927 | *Bifidobacterium longum* subsp *longum* JDM 301 |
| gi\|296182928 | *Bifidobacterium longum* subsp *longum* JDM 301 |
| gi\|283103603 | *Bifidobacterium dentium* Bd1 |
| gi\|190713109 | *Lactobacillus casei* BL23 |
| gi\|190713871 | *Lactobacillus casei* BL23 |
| gi\|190713978 | *Lactobacillus casei* BL23 |

The enzymatic fucosylation reaction according to step d) provides a compound of formula 10B and salts thereof

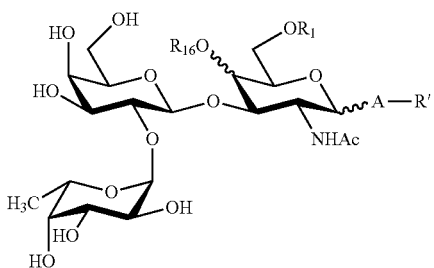

wherein R', $R_1$, $R_{16}$ and A are as defined above.

In step d) the enzymes comprising transsialidase or transfucosidase activity as defined above may also comprise engineered enzymes comprising transsialidase or transfucosidase activity. It is particularly envisaged that wild type or mutated glycosidases displaying α-transsialidase or α-transfucosidase activity can be used in the present invention to produce the target oligosaccharides. Preparation of such enzymes is preferably carried out via site directed mutagenesis approaches or directed evolution.

In rational engineering novel altered enzymes (mutants) are created via site directed mutagenesis approaches, preferably by introduction of point mutations. This technique generally requires reliance on the static 3D protein structure. The mutations generally affect the active site of the enzymes such that they lose their ability to degrade their transglycosylation products but remain capable of synthesis. A preferred strategy consists of the replacement of the catalytic nucleophile by a non-nucleophilic residue. This modification results in the formation of an inactive mutant or an altered enzyme with reduced transglycosylation activity due the lack of appropriate environment for the formation of the reactive host-guest complex for transglycosylation. However, in the presence of a more active glycosyl donor (e.g. fucosyl fluoride) that mimics the glycosyl enzyme intermediate, the mutated enzyme is able to transfer efficiently the glycosyl moiety to a suitable acceptor generating a glycoside with inverted anomeric stereochemistry. Such a mutant glycosidase is termed as glycosynthase (e.g. fucosynthase) and their development represents one of the major advances in the use of glycosidases for synthetic purposes. In principle, the glycosynthase concept can be applied to all GH specificities and offer a large panel of enzymes potentially able to synthesize various oligosaccharides with very high yields, up to 95%.

The second preferred technique is called directed evolution. This strategy comprises random mutagenesis applied to the gene of the selected glycosidase and generates thus a library of genetically diverse genes expressing glycosidase. Generation of sequence diversity can be performed using well-known methodologies, the most preferable being the error prone polymerase chain reaction (epCR) method. This gene library may be inserted into suitable microorganisms such as *E. coli* or *S. cerevisiae* for producing recombinant variants with slightly altered properties. Clones expressing improved enzymes are then identified with a fast and reliable screening method, selected and brought into a next round of mutation process. The recursive cycles of mutation, recombination and selection are continued as far as mutant(s) with the desired activity and/or specificity is/are evolved. To date, different high-throughput screening methodologies for glycosidases including glycosynthases have been developed. Applying these approaches, effective engineered transglycosidases, including new and more efficient glycosynthases can and have been created and isolated. An α-L-fucosidase from *Thermotoga maritima* has been recently converted into an efficient α-L-transfucosidase by directed evolution. The transferase/hydrolysis ratio of the evolved enzyme was 30 times higher than the native enzyme (see Osanjo et al. *Biochemistry* 46, 1022 (2007)).

Proteins comprising a transglycosidase and/or a glycosynthase activity as defined above may also comprise fragments or variants of those protein sequences. Such fragments or variants may typically comprise a sequence having a sequence identity with one of the above mentioned proteins sequences of at least 70%, more preferably at least 80%, equally more preferably at least 85%, even more preferably at least 90% and most preferably at least 95% or even 97%, 98% or 99% as compared to the entire wild type sequence on amino acid level.

"Fragments" of proteins or peptides in the context of the present invention may also comprise a sequence of a protein or peptide as defined herein, which is, with regard to its amino acid sequence N-terminally, C-terminally and/or intrasequentially truncated compared to the amino acid sequence of the original (native) protein. Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Likewise, "fragments" of nucleic acids in the context of the present invention may comprise a sequence of a nucleic acid as defined herein, which is, with regard to its nucleic acid molecule 5'-, 3'- and/or intrasequentially truncated compared to the nucleic acid molecule of the original (native) nucleic acid molecule. A sequence identity with respect to such a fragment as defined herein may therefore preferably refer to the entire nucleic acid as defined herein.

"Variants" of proteins or peptides as defined in the context of the present invention (e.g. as encoded by a nucleic acid as defined herein) may be encoded by the nucleic acid molecule of a polymeric carrier cargo complex. Thereby, a protein or peptide may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property.

"Variants" of proteins or peptides as defined in the context of the present invention (e.g. as encoded by a nucleic acid as defined herein) may also comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. *Proc. Natl. Acad. Sci. USA* 90, 5873 (1993) or Altschul et al. *Nucleic Acids Res.* 25, 3389 (1997). Such an algorithm is integrated in the BLAST program. Sequences which are identical to the sequences of the present invention to a certain extent can be identified by this program.

The enzymes used in step d) may be provided in a free form or alternatively be bound to or are immobilized onto a surface. Binding to or immobilization onto a surface may be carried out e.g. via electrostatic bonds, van der Waals-bonds, covalent bonds, etc. Binding to or immobilization onto a surface may be furthermore carried out, using a covalent linker or a crosslinker, or a tag, as known to a skilled person for purification of proteins. Such tags comprise, inter alia, e.g. affinity tags or chromatography tags. Affinity tags may include e.g. chitin binding protein (CBP), maltose binding protein (MBP), glutathione-S-transferase (GST), or the Strep-Tag. The poly(His) tag is a widely-used protein tag, that binds to metal matrices. Chromatography tags are used to alter chromatographic properties of the protein to afford different resolution across a particular separation technique, and include e.g. polyanionic amino acids based tags, such as the FLAG-tag. The surface may be the surface of a bioreactor, or any suitable reaction chamber.

The enzymatic reaction can be carried out as described in WO 2012/007588, WO 2012/127410 or WO 2012/156897, preferably occurs with a concentration of respective enzyme in a concentration of 1 mU/l to 1000 U/l, preferably 10 mU/l to 100 U/l, when the activity capable of forming 1 μmol of specific product for a defined protein starting from a defined educt is defined as 1 unit (U), e.g. for a glycotransferase the production of a glycose-containing complex carbohydrate at 37° C. in 1 minute. The activity of each enzyme as defined herein may be assessed with respect to its naturally occurring or engineered substrate. The incubation may be carried out in a reaction medium, preferably an aqueous medium, comprising the compound obtained according to step c) and optionally water; a buffer such as a phosphate buffer, a carbonate buffer, an acetate buffer, a borate buffer, a citrate buffer and a tris buffer, or combinations thereof; alcohol, such as methanol and ethanol; ester such as ethyl acetate; ketone such as acetone; amide such as acetamide; and the like. Furthermore, the incubation may be carried out in a reaction medium as defined above, wherein optionally a surfactant or an organic solvent may be added, if necessary. Any surfactant capable of accelerating the formation of a complex carbohydrate as defined according to the present invention as a possible product of the invention can be used as the surfactant. Examples include non-ionic surfactants such as polyoxyethylene octadecylamine (e.g., Nymeen S-215, manufactured by Nippon Oil & Fats); cationic surfactants, such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant may be used generally in a concentration of 0.1 to 50 g/l. The organic solvent may include xylene, toluene, fatty acid alcohol, acetone, ethyl acetate, and the like, which may be used in a concentration of generally 0.1 to 50 ml/l.

The incubation may be furthermore carried out in a reaction medium as defined above, preferably having a pH 3 to 10, pH 5 to 10, preferably pH 6 to 8.

The incubation may be furthermore carried out at a temperature of about 0° C. to about 100° C., preferably at a temperature of about 10 to about 50° C., e.g. at a temperature of about 20° C. to about 50° C. In the reaction medium, inorganic salts, such as $MnCl_2$ and $MgCl_2$, may be added, if necessary.

The incubation according to step d) of the method of the present invention may be carried out in a bioreactor. The bioreactor is preferably suitable for either a continuous mode or a discontinuous mode. If carried out in a continuous mode, the method preferably provides for a continuous flow of compounds and/or enzymes as necessary, preferably by continuously providing educts of the reaction to the reaction mixture and continuously removing products from the reaction mixture, while maintaining the concentration of all components, including enzymes at a predetermined level. The enzymes used in a continuous mode may be added either in free form or as bound or immobilized to a surface.

In the optional step e) of the present invention a compound obtained in step c) or step d) is subjected to catalytic hydrogenolysis and/or anomeric deprotection.

Accordingly, the catalytic hydrogenolysis is performed when, in a compound of formula 7 obtained in step c) or in a compound of formula 10 obtained in step d), R' is —$N_3$ or —$OR'_6$ wherein $R'_6$ is a group removable by hydrogenolysis or —$(CH_2)_n$—$N_3$, or when $R_{16}$ is a moiety C wherein at least one of the $R_{17}$ and $R_{18}$ groups is a group removable by hydrogenolysis and R' is 2-trimethylsilyl-ethyloxy. Such catalytic hydrogenolysis typically takes place in a protic solvent or in a mixture of protic solvents. A protic solvent may be selected from the group consisting of water, acetic acid or $C_1$-$C_6$ alcohols. A mixture of one or more protic solvents with one or more suitable aprotic organic solvents partially or fully miscible with the protic solvent(s) (such as THF, dioxane, ethyl acetate or acetone) may also be used. Water, one or more $C_1$-$C_6$ alcohols or a mixture of water and one or more $C_1$-$C_6$ alcohols are preferably used as the solvent system. Solutions containing the carbohydrate derivatives in any concentration or suspensions of the carbohydrate derivatives in the solvent(s) used are also applicable. The reaction mixture is stirred at a temperature in the range of 10-100° C., preferably between 20-50° C., in a hydrogen atmosphere of 1-50 bar absolute (100 to 5000 kPa) in the presence of a catalyst such as palladium, Raney nickel or any other appropriate metal catalyst, preferably palladium on charcoal or palladium black, until reaching the completion of the reaction. Transfer hydrogenolysis may also be performed, when the hydrogen is generated in situ from cyclohexene, cyclohexadiene, formic acid or ammonium formate. Addition of organic or inorganic bases or acids and/or basic and/or acidic ion exchange resins can also be used to improve the kinetics of the hydrogenolysis. The conditions proposed above allow simple, convenient and delicate removal of benzyl-like protective groups giving rise to a group of compound of formula 1 wherein R is OH (from compounds of formula 7 or 10 wherein R' is —$N_3$ or —$OR'_6$ wherein $R'_6$ a group removable by hydrogenolysis), or R is —O—$(CH_2)_n$—$NH_2$ (from compounds of formula 7 or 10 wherein R' is —$(CH_2)_n$—$N_3$), or to another group of compounds of formula 1 wherein R is 2-trimethylsilyl-ethyloxy and $R_2$ is fucosyl moiety (from compounds of formula 7 or 10 wherein R' 2-trimethylsilyl-ethyloxy and $R_{16}$ is a moiety C wherein at least one of the $R_{17}$ and $R_{18}$ groups is a group removable by hydrogenolysis). It should be noted that that anomeric azide group (R' is —$N_3$) in a the above-mentioned compounds of formula 7 or 10 is reduced to amino under the conditions disclosed above, and the thus formed glycosyl amine easily undergoes hydrolysis to give the anomerically unprotected compound of formula 1 (R is OH). Similarly, R'=—O—$(CH_2)_n$—$N_3$ in a compound of formula 7 or 10 is converted to —O—$(CH_2)_n$—$NH_2$ under these conditions.

Also optionally in step e), R' group being —$N_3$ or —$OR'_6$ wherein $R'_6$ is selected from 2-trimethylsilyl-ethyl or allyl optionally substituted by one or more methyl in a compound of formula 7 or 10 obtained in step c) or d)—provided that in moiety C, if it is present in a compound of formula 7 or 10, both $R_{17}$ and $R_{18}$ groups are H—can be converted to OH in an anomeric deprotection reaction. In an embodiment, the R' group being —$N_3$ in a compound of formula 7 or 10 can be reduced by complex metal hydrides like $NaBH_4$, or by $PPh_3$ or Cu/Zn. Both types of reactions yield amine functionality at the anomeric position, the hydrolysis of which under neutral or slightly acidic pH (pH 4-7) readily provides the fully deprotected oligosaccharides of formula 1 wherein R is —OH. In other embodiment, allyl glycosides (R' is —$OR'_6$ wherein $R'_6$ is allyl optionally substituted by one or more methyl) can be removed in a delicate way by a) isomerization with Pd-, Rh- or Ir-complex catalyst followed by mild hydrolysis of the resulting 1-propenyl glycoside, or b) using Pd(0) or Ni(0) catalyst. 2-Trimethylsilyl-ethyl glycosides (R' is —$OR'_6$ wherein $R'_6$ is 2-trimethylsilyl-ethyl) can be deprotected with fluoride ion (from $BF_4^-$), an anion of a strong acid (e.g. trifluoroacetate) or a Lewis-acid ($BF_3$-etherate, $ZnCl_2$, $SnCl_4$, $FeCl_3$) followed by careful hydrolysis of the resulting glycosyloxy derivative substituted with the remains of the reagent that is used (see Jansson et al. J. Org. Chem. 53, 5629 (1988)). In compounds of formula 10 wherein R' is —$N_3$ or —$OR'_6$ wherein $R'_6$ is selected from allyl optionally substituted by one or more methyl or 2-trimethylsilyl-ethyl, and in moiety C at least one of the $R_{17}$ and $R_{18}$ groups is a group removable by hydrogenolysis, the anomeric deprotection reaction is followed by catalytic hydrogenolysis to give compounds of formula 1 wherein R is —OH and $R_2$ is fucosyl moiety.

Thus, in accordance with the present invention, complex 3-O-galactosyl-GlcNAc or -GalNAc derivatives of formula 1 and salts thereof

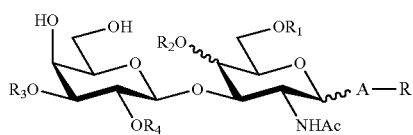

wherein R is selected from —OH, —$N_3$ and —$OR_6$ wherein $R_6$ is selected from allyl optionally substituted by one or more methyl, propargyl optionally substituted by one or more methyl, 2-trimethylsilyl-ethyl-$(CH_2)_n$—$NH_2$ and —$(CH_2)_n$—$N_3$ wherein integer n is 1 to 10, preferably 2 or 3, $R_1$ is selected from sialyl moiety, —$SO_3H$ and —$CH(R_5)$—COOH wherein $R_5$ is selected from H, alkyl and benzyl, $R_2$ is selected from H and fucosyl moiety, $R_3$ is selected from H and sialyl moiety, $R_4$ is selected from H and fucosyl moiety, provided that at least one of $R_3$ and $R_4$ is H, and A is a divalent carbohydrate linker, can be effectively synthesized. Both the anomerically deprotected derivatives (R is —OH), and the glycosides listed above have synthetic usefulness. The unsaturated bond of glycosides having —$N_3$, —O—$(CH_2)_n$—$N_3$, —O-allyl or —O-propargyl aglycon or the —O—$(CH_2)_n$—$NH_2$ group can be functionalized by a wide variety of selective and mild water-compatible chemical reactions. Thus e.g. the azido group of a compound of formula 1 can be brought into "click chemistry" with an alkyne to form bioconjugates (and so can the propargyl derivatives of formula 1 with an azido reagents). The allyl functionality can be converted to other functional groups by addition reactions to the double bond or by ozonolysis. The amino function can be used to make amide or urea linkage to bind a compound of formula 1 to (bio)macromolecules/polymers.

The present method readily provides the synthesis of complex sialylated and/or fucosylated 3'-O-galactosyl-6-O-sialyl-GlcNAc or -GalNAc derivatives, glycosides and analogs thereof, by a unique combination of chemical and enzymatic glycosylation steps in the reaction sequence. The process opens the possibility, via the permutation of the mandatory and optional glycosylation steps, to obtain a number of compounds being substituted by sialyl and/or fucosyl moiety/moieties in various positions. These possible substitution patterns are summarized in Table 4 below.

charide derivative first to obtain a sialyl-galactose disaccharide that—after transforming it to a disaccharide donor—was used to glycosylate the GlcNAc acceptor, often with unsatisfactory regioselectivity. The present method however avoids the fabrication and use of this type of difficult to obtain disaccharide donor, and instead introduces a direct enzymatic sialylation of intermediates of formula 7 obtained in step c) of the present method that takes place with good regio- and stereoselectivity. Additionally, the intermediate of formula 7 can be a substrate for enzymatic fucosylation as well, and therefore the method provides a diverse group of variously sialylated and/or fucosylated 3'-O-galactosyl-6-O-sialyl-GlcNAc or -GalNAc derivatives and analogs thereof.

Within the first aspect of the invention the synthesis of compounds of formula 1 wherein A is a divalent lactosyl linker is preferred. More preferably, compounds of formula 1 are human milk oligosaccharides listed in Table 1 above and derivatives, even more preferably LST b, F-LST b, DS-LNT or FDS-LNT I and derivatives. Accordingly, a compound of formula 2A falling into the scope of compounds of formula 2

TABLE 4

| step a) | step b) | step d) | substitution pattern |
|---|---|---|---|
| sialylation at 6 | — | — | 6-O-sialyl |
| sialylation at 6 | — | sialylation at 3' | 3',6-di-O-sialyl |
| sialylation at 6 | fucosylation at 4 | — | 4-O-fucosyl-6-O-sialyl |
| sialylation at 6 | fucosylation at 4 | sialylation at 3' | 4-O-fucosyl-3',6-di-O-sialyl |
| sialylation at 6 | — | fucosylation at 2' | 2'-O-fucosyl-6-O-sialyl |
| sialylation at 6 | fucosylation at 4 | fucosylation at 2' | 2',4-di-O-fucosyl-6-O-sialyl |

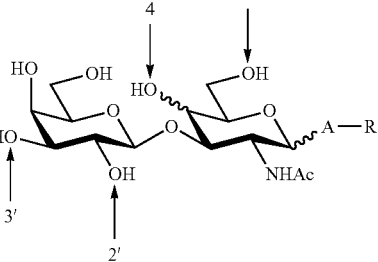

In addition, it has shown that the sialyl residue at position 6 can be replaced by simpler charged residues like carboxymethyl or sulfate while maintaining the the biological effect of the parent sialylated compounds (see e.g. Chachadi et al. *Glycoconj. J.* 28, 49 (2011), WO 2011/130332, Liao et al. *J. Am. Chem. Soc.* 132, 14849 (2010), Wang et al. *Proc. Nat. Acad. Sci. USA* 106, 18137 (2009), Schwardt et al. *J. Med. Chem.* 52, 989 (2009)). The method disclosed above gives the opportunity for the synthesis of these kinds of analogs as well when the chemical sialylation in step a) is replaced by a chemical carboxymethylation or sulfation.

Moreover, the present method is advantageous in that these various groups of compounds can be available in a simpler manner and/or in fewer steps. Ando et al. (*Carbohydr. Res.* 338, 503 (2003)) taught that 6-O-sialylation of "bulky" acceptors where the OH— group to be sialylated belonged to an internal GlcNAc residue was not favourable because only low yields could be achieved. Therefore it was proposed to sialylate acceptors having a terminal GlcNAc moiety. However the present inventors found that compounds of formula 2 having an internal GlcNAc can be sialylated effectively. In addition, Ando et al. *J. Carbohydr. Chem.* 20, 425 (2001) and *Carbohydr. Res.* 338, 503 (2003), reported the introduction of the 3'-O-sialyl moiety in an indirect way, that is by sialylation of a galactose monosac-

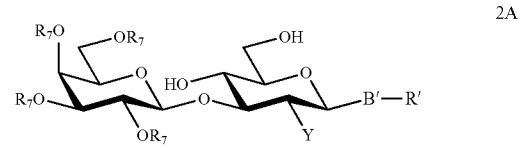

wherein Y and $R_7$ are as defined above,

R' is as defined above, preferably R' is OR" wherein R" is a group removable by hydrogenolysis, and B' is a divalent lactosyl moiety having the R' group on its C-1 anomeric carbon atom and attached via its 3'—OH group to the lacto-N-biose residue of the compound of formula 2A, optionally substituted by a fucosyl moiety on its 3-OH or by a N-acetyllactosaminyl moiety on its 6'-OH, which N-acetyllactosaminyl moiety can optionally be further substituted by an N-acetylneuraminyl moiety on its 6-OH, or by a fucosyl on its 3-OH or 2'-OH, and the functional groups of the divalent lactosyl residue B' are protected, preferably the free OH groups are acylated (e.g acetylated, benzoylated) and the carboxy group of the optional N-acetylneuraminyl moiety is blocked in ester form (e.g. methyl, ethyl or benzyl ester), except for the the axial 4-OH— group of any galactosyl moiety in group B' that is optionally protected,
is sialylated, sulfated or carboxymethylated in step a) giving a compound of formula 4D

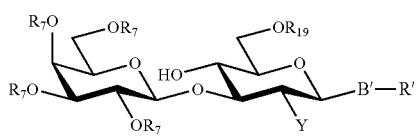

4D wherein R', B', Y and $R_7$ are as defined above, and
$R_{19}$ is selected from —$SO_3H$, —$CH(R_5)$—$COOR_{10}$ and moiety H

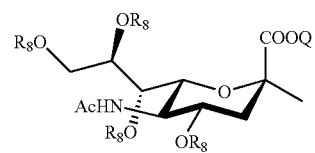

H wherein $R_5$, $R_8$ and Q are as defined above.
Preferably a compound of formula 2A

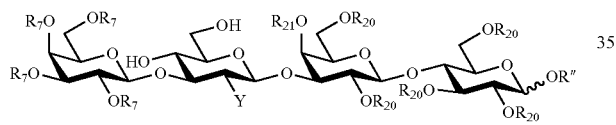

2A wherein R", Y and $R_7$ are as defined above,
$R_{20}$ is independently acyl, and
$R_{21}$ is selected from H and acyl,
more preferably a compound of formula 2A wherein Y is selected from —NHAc and trichloroacetamido, the $R_7$ groups are identical and selected from acetyl, benzoyl and 4-chlorobenzoyl, the $R_{20}$ groups are identical and selected from acetyl, benzoyl and 4-chlorobenzoyl, and $R_{21}$ is selected from H, acetyl, benzoyl or 4-chlorobenzoyl, is reacted with a sialyl donor of formula 3 defined above to give a compound of formula 4E

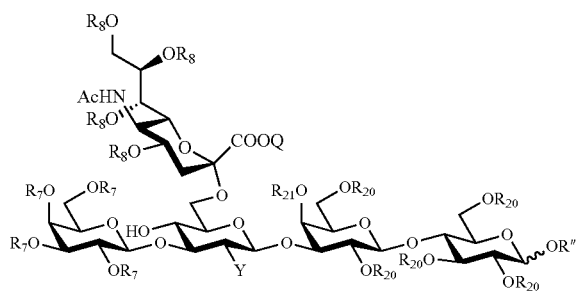

4E wherein R" is a group removable by hydrogenolysis,
Y is selected from —NHAc, haloalkanoylamido, —$NAc_2$, haloalkoxycarbonylamino, 2,3-diphenylmaleimido, 2,3-dimethylmaleimido and azido, preferably —NHAc and trichloroacetamido, $R_7$ is independently acyl, preferably the $R_7$ groups are identical and selected from acetyl, benzoyl and 4-chlorobenzoyl, $R_8$ is independently acyl, preferably the $R_8$ groups are acetyl, $R_{20}$ is independently acyl, preferably the $R_{20}$ groups are identical and selected from acetyl, benzoyl and 4-chlorobenzoyl, $R_{21}$ is selected from H and acyl, preferably $R_{21}$ is selected from H, acetyl, benzoyl or 4-chlorobenzoyl, and Q is selected from alkyl and benzyl, preferably methyl, ethyl and benzyl.

In the subsequent step b) a compound of formula 4D, preferably of formula 4E, is optionally fucosylated with a fucosyl donor of formula 5A

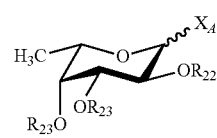

5A wherein $X_A$ is selected from alkylthio and optionally substituted phenylthio, preferably —SPh, $R_{22}$ and $R_{23}$ are, independently, selected from a group removable by hydrogenolysis and acyl (preferably acetyl, pivaloyl, benzoyl and 4-chlorobenzoyl), to give rise to a compound of formula 6D

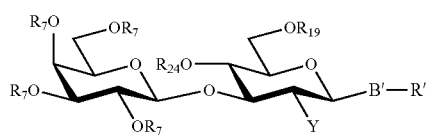

6D wherein R', B', Y, $R_7$ and $R_{19}$ are as defined above, and
$R_{24}$ is a moiety I

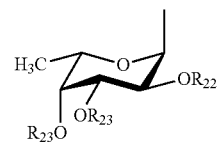

I wherein $R_{22}$ and $R_{23}$ are as defined above,
Preferably, a compound of formula 6D is represented by the formula 6E

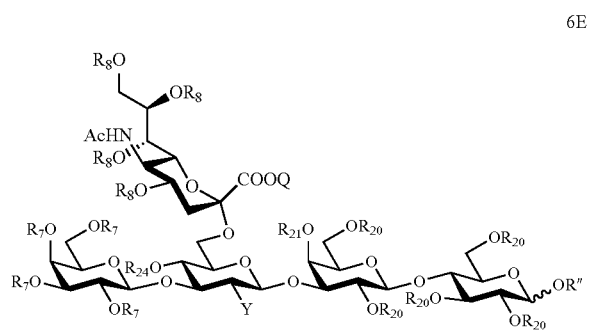

6E wherein R" is a group removable by hydrogenolysis,

Y is selected from —NHAc, haloalkanoylamido, —NAc$_2$, haloalkoxycarbonylamino, 2,3-diphenylmaleimido, 2,3-dimethylmaleimido and azido, preferably —NHAc and trichloroacetamido, R$_7$ is independently acyl, preferably the R$_7$ groups are identical and selected from acetyl, benzoyl and 4-chlorobenzoyl, R$_8$ is independently acyl, preferably the R$_8$ groups are acetyl, R$_{20}$ is independently acyl, preferably the R$_{20}$ groups are identical and selected from acetyl, benzoyl and 4-chlorobenzoyl, R$_{21}$ is selected from H and acyl, preferably R$_{21}$ is selected from H, acetyl, benzoyl or 4-chlorobenzoyl, and Q is selected from alkyl and benzyl, preferably methyl, ethyl and benzyl, and R$_{24}$ is moiety I as defined above.

In the subsequent step c) a compound of formula 4D obtained in step a) or a compound of formula 6D obtained in step b) is subjected to deprotective treatment and optional transformation of Y to —NHAc to result in the formation of a compound of formula 7A

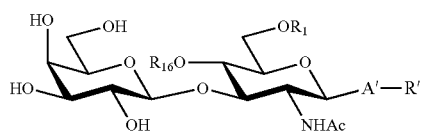

7A wherein R' is as defined above, moiety A' is a divalent lactosyl moiety having the R' group on its C-1 anomeric carbon atom and attached via its 3'—OH group to the lacto-N-biose residue of the compound of formula 7A, optionally substituted by a fucosyl moiety on its 3-OH or by a N-acetyllactosaminyl moiety on its 6'-OH, which N-acetyllactosaminyl moiety can optionally be further substituted by an N-acetylneuraminyl moiety on its 6-OH, or by a fucosyl on its 3-OH or 2'-OH, moiety A' being devoid of any OH-protective groups and the ester protective group of the N-acetyl neuraminyl moiety (if present), R$_1$ is selected from sialyl, —SO$_3$H and —CH(R$_5$)—COOH, wherein R$_5$ is as defined above, and R$_{16}$ is selected from H and a moiety of formula C

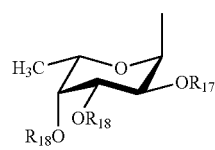

C wherein R$_{17}$ and R$_{18}$, independently, are selected from H and a group removable by hydrogenolysis, comprising the steps of
i) base catalysed transesterification to remove O-acyl groups,
ii) basic hydrolysis,
iii) and optional transformation of Y to —NHAc.

Alternatively, the base catalysed transesterification deprotection can be avoided and the O-acyl groups can be removed by basic hydrolysis.

Preferably, in this step c) of the method a compound of formula 4E or a compound of formula 6E defined above is converted into a compound of formula 7B

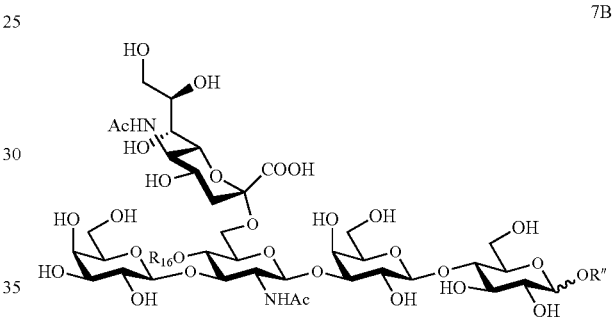

7B wherein R" is a group removable by hydrogenolysis, and R$_{16}$ is selected from H and moiety C defined above, preferably H comprising:
i) base catalysed transesterification deprotection, preferably NaOMe/MeOH treatment,
ii) basic hydrolysis, preferably NaOH/MeOH treatment, and
iii) where group Y in a compound of formula 4E or 6E selected from haloalkanoylamido, haloalkoxycarbonylamino, 2,3-diphenylmaleimido, 2,3-dimethylmaleimido and azido, preferably trichloroacetamido, is deprotected to amino under the conditions used in step ii) or by other azido-amino transformations disclosed above, selective N-acetylation or peracetylation/de-O-acetylation.

Still within the preferred embodiment of the method, in step d), a compound of formula 7A is optionally sialylated or fucosylated under the action of a sialidase or fucosidase having transsialidase or transfucosidase/fucosynthase activity, respectively, to give a compound of formula 10C

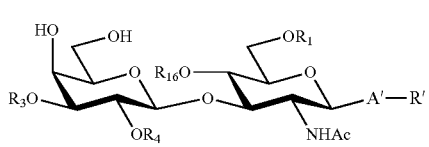

10C wherein R', A', $R_1$, and $R_{16}$ are as defined above,
$R_3$ is selected from H and a sialyl, and
$R_4$ is selected from H and fucosyl moiety, provided that one but only one of $R_3$ and $R_4$ is H.

Particularly, a compound according to formula 7B can be reacted with a sialyl donor, preferably a N-acetyl neuraminyl donor selected from 3'-O-sialyllactose or p-nitrophenyl N-acetyl-α-neuraminoside in the presence of transsialidase, preferably a transsialidase listed in Table 2 above, to make a compound of formula 10D

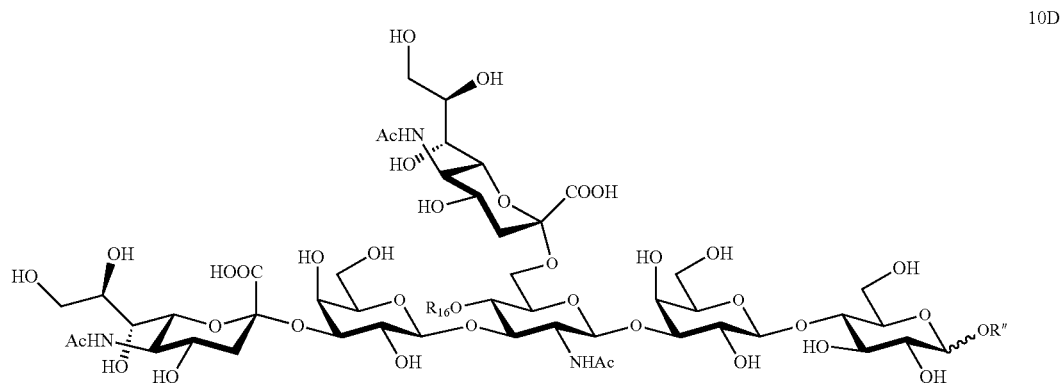

10D wherein R" and $R_{16}$ are as defined above.

With regard to the optional enzymatic fucosylation in this step d) of the claimed method, a compound of formula 7A, preferably of formula 7B, can be subjected to enzymatic fucosylation under the action of a fucosidase having trans-fucosidase/fucosynthase activity, preferably those listed in Table 3, in the presence of a fucosyl donor selected from 2-O-fucosyllactose or fucosyl fluoride to give a compound of formula 10E oligosaccharides of formula 1A and analogs thereof, preferably human milk oligosaccharides listed in Table 1 above or analogs

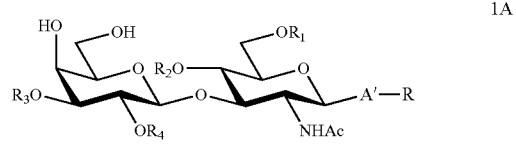

1A

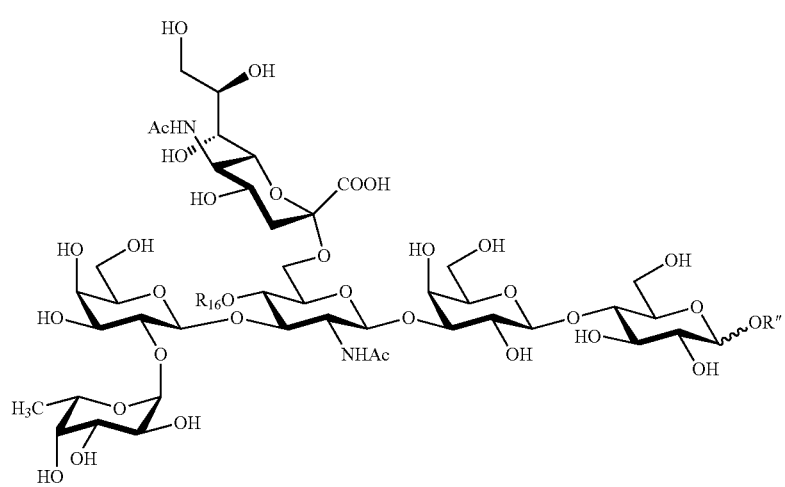

10E wherein R" and $R_{16}$ are as defined above.

Finally in step e), if it is desired, a compound of formula 7A or 10C is subjected to catalytic hydrogenation to remove benzyl/substituted benzyl protective group(s) or to an anomeric deprotection method described above to give complex wherein A', R, $R_1$, $R_2$, $R_3$ and $R_4$ are as defined above, provided that at least one of $R_3$ and $R_4$ is H.

Preferably, the hydrogenolysis of a compound of formula 10D provides a compound of formula 1B

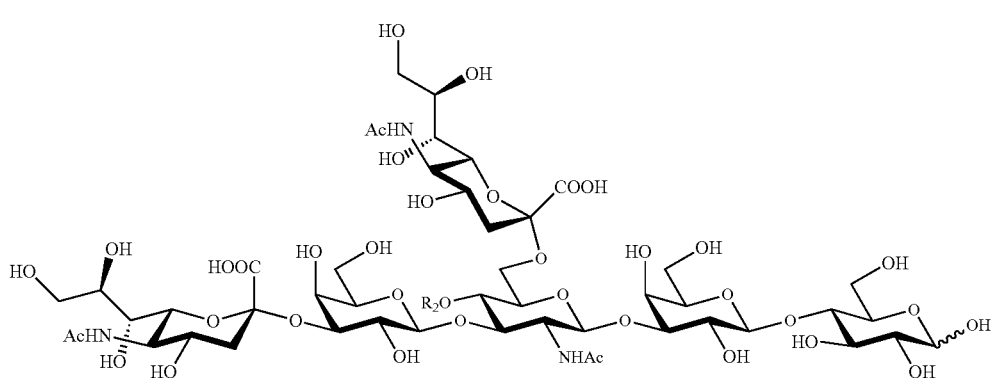

1B wherein $R_2$ is selected from H and fucosyl,
that is DS-LNT and FDS-LNT I, respectively. Similarly, from a compound of formula 10E defined above a compound of formula 1C

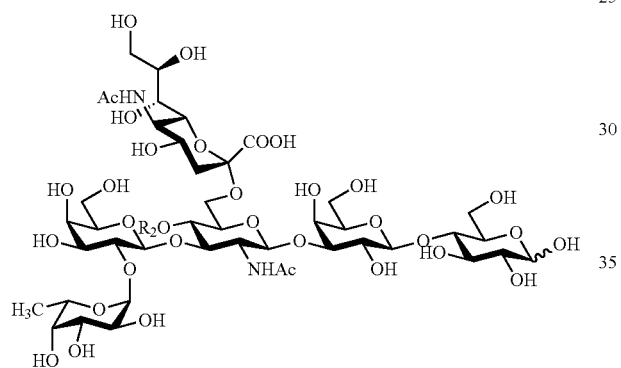

1C wherein $R_2$ is as defined above,
is easily accessible. Preferably, $R_2$ is H in a compound of formula 1C that corresponds to F-LST b.

Also preferably, the catalytic hydrogenolysis of a compound of formula 7B readily provides a compound of formula 1D

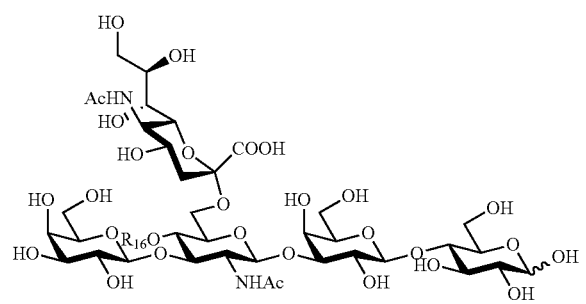

1D wherein $R_{16}$ is as defined above, preferably H (corresponding to LST b).

The method according to the first aspect of the invention involves useful novel synthetic intermediates for the synthesis of sialylated/fucosylated oligosaccharides and their analogs. Thus the second aspect of the invention provides a compound of formula 11 and salts thereof

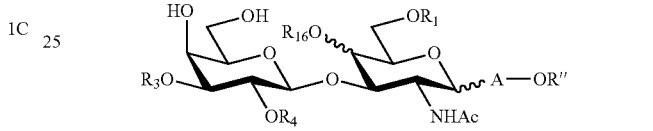

11 wherein R" is a group removable by hydrogenolysis,

A is a divalent carbohydrate linker as defined above, $R_1$ is selected from sialyl moiety, —$SO_3H$ and —CH($R_5$)—COOH wherein $R_5$ is selected from H, alkyl and benzyl, $R_3$ is selected from H and sialyl moiety, $R_4$ is selected from H and fucosyl moiety, provided that at least one of $R_3$ and $R_4$ is H, and $R_{16}$ is selected from H and moiety C, preferably H,

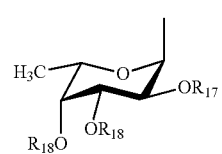

C wherein $R_{17}$ and $R_{18}$, independently, are selected from H and a group removable by hydrogenolysis.

A compound of formula 11 can be either an α- or β-anomer or an anomeric mixture of α- and β-anomers. It can be crystalline solid, oil, syrup, precipitated amorphous material or spray dried product. If crystalline, a compound of formula 11 could exist either in an anhydrous or hydrated crystalline form by incorporating one or several molecules of water into its crystal structure. Likewise, a compound of formula 11 could exist as a crystalline substance, incorporating ligands such as organic molecules and/or ions into its crystal structure.

A preferred compound of formula 11 is a compound of formula 11A being a precursor for DS-LNT, FDS-LNT I, F-LST b, LST b and analogs thereof

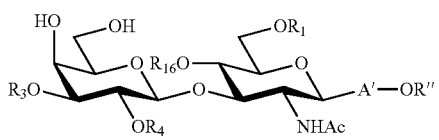

11A wherein R", $R_1$, $R_3$, $R_4$ and $R_{16}$ are as defined above, provided that at least one of $R_3$ and $R_4$ is H, and A' is a divalent lactosyl moiety having the —OR" group on its C-1 anomeric carbon atom and attached via its 3'—OH group to the lacto-N-biose residue of the compound of formula 11A, optionally substituted by a fucosyl moiety on its 3-OH or by a N-acetyllactosaminyl moiety on its 6'-OH, which N-acetyllactosaminyl moiety can optionally be further substituted by an N-acetylneuraminyl moiety on its 6-OH, or by a fucosyl on its 3-OH or 2'-OH, moiety A' being devoid of any OH-protective groups and the ester protective group of the N-acetyl neuraminyl moiety (if present), particularly a compound of formula 10D

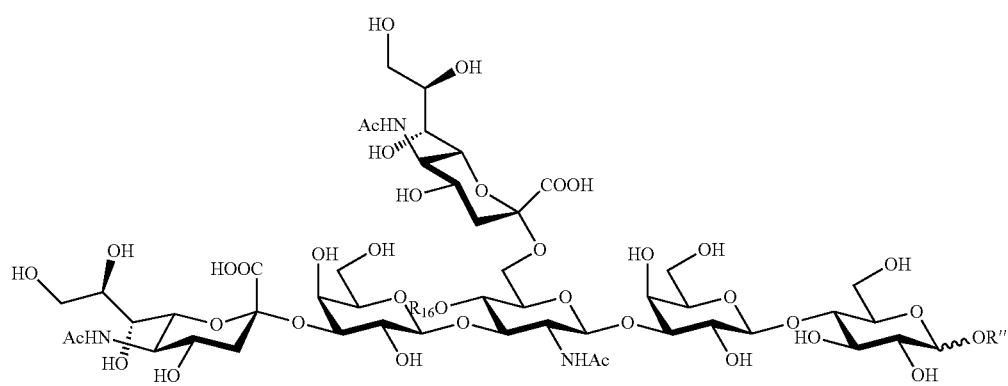

10D wherein R" and $R_{16}$ are as defined above,
and also particularly a compound of formula 10E

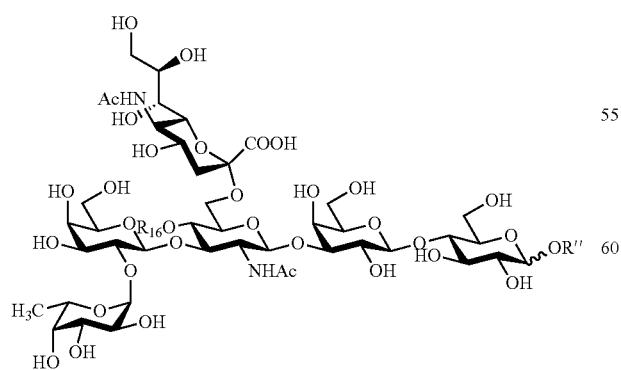

10E wherein R" and $R_{16}$ are as defined above.

In another preferred embodiment a compound of formula 11A is characterized by formula 7C

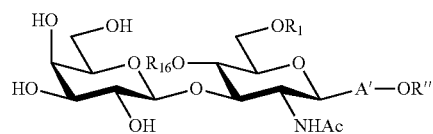

7C wherein R", A', $R_1$ and $R_{16}$ are as defined above.

A preferred compound of formula 7C is a compound of formula 7B

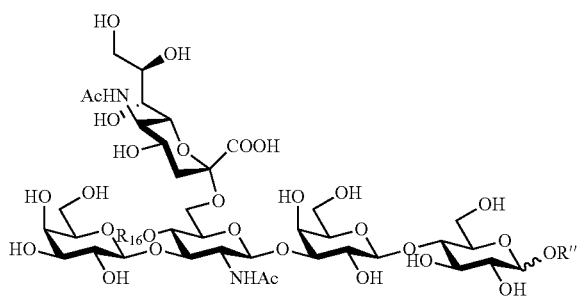

7B wherein R" is a group removable by hydrogenolysis, and $R_{16}$ is selected from H and moiety C defined above, preferably H.

The third aspect of the invention relates to the precursors of compounds of formula 11 defined above in the synthetic process claimed, that are characterized by formula 12

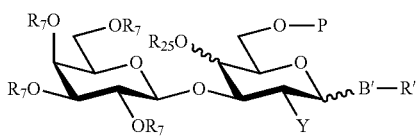

12 wherein R' is selected from —N$_3$ and —OR'$_6$ wherein R'$_6$ is selected from allyl optionally substituted by one or more methyl, propargyl optionally substituted by one or more methyl, a group removable by hydrogenolysis, 2-trimethylsilyl-ethyl and —(CH$_2$)$_n$—N$_3$ wherein integer n is 1 to 10, preferably 2 or 3, R$_7$ is independently acyl, Y is selected from —NHAc, haloalkanoylamido, —NAc$_2$, haloalkoxycarbonylamino, 2,3-diphenylmaleimido, 2,3-dimethylmaleimido and —N$_3$, and B' is a divalent lactosyl linker in protected form, that is B' is a divalent lactosyl moiety having the R' group on its C-1 anomeric carbon atom and attached via its 3'—OH group to the lacto-N-biose residue of the compound of formula 12, optionally substituted by a fucosyl moiety on its 3-OH or by a N-acetyllactosaminyl moiety on its 6'-OH, which N-acetyllactosaminyl moiety can optionally be further substituted by an N-acetylneuraminyl moiety on its 6-OH, or by a fucosyl on its 3-OH or 2'-OH, and the functional groups of the divalent lactosyl residue B' are protected, preferably the free OH groups are acylated (e.g acetylated, benzoylated) and the carboxy group of the optional N-acetylneuraminyl moiety is blocked in ester form (e.g. methyl, ethyl or benzyl ester), except for the the axial 4-OH— group of any galactosyl moiety in group B' that is optionally protected, P is selected from protected sialyl moiety, —SO$_3$H and —CH(R$_5$)—COOR$_{10}$ wherein R$_5$ is selected from H, alkyl and benzyl, R$_{10}$ is selected from alkyl and benzyl, and R$_{25}$ is selected from moiety I and H, preferably H,

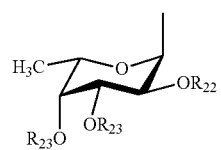

I wherein R$_{22}$ and R$_{23}$ are, independently, selected from a group removable by hydrogenolysis and acyl (preferably acetyl, pivaloyl, benzoyl or 4-chlorobenzoyl).

A compound of formula 12 can be either an α- or β-anomer or an anomeric mixture of α- and β-anomers. It can be crystalline solid, oil, syrup, precipitated amorphous material or spray dried product. If crystalline, a compound of formula 12 can exist either in an anhydrous or hydrated crystalline form by incorporating one or several molecules of water into its crystal structure. Likewise, a compound of formula 12 can exist as a crystalline substance, incorporating ligands such as organic molecules and/or ions into its crystal structure.

The preferred precursors of compounds of formula 12 are defined by formula 12A

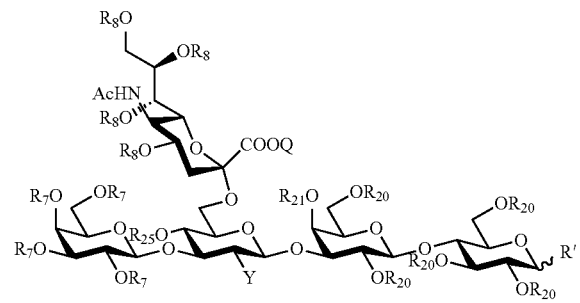

12A wherein R' and R$_{25}$ are as defined above,

Y is selected from —NHAc, haloalkanoylamido, —NAc$_2$, haloalkoxycarbonylamino, 2,3-diphenylmaleimido, 2,3-dimethylmaleimido and azido, preferably —NHAc and trichloroacetamido, R$_7$ is independently acyl, preferably the R$_7$ groups are identical and selected from acetyl, benzoyl and 4-chlorobenzoyl, R$_8$ is independently acyl, preferably the R$_8$ groups are acetyl, R$_{20}$ is independently acyl, preferably the R$_{20}$ groups are identical and selected from acetyl, benzoyl and 4-chlorobenzoyl, R$_{21}$ is selected from H and acyl, preferably R$_{21}$ is selected from H, acetyl, benzoyl or 4-chlorobenzoyl, and Q is selected from alkyl and benzyl, preferably methyl, ethyl and benzyl, more preferably by formula 4E

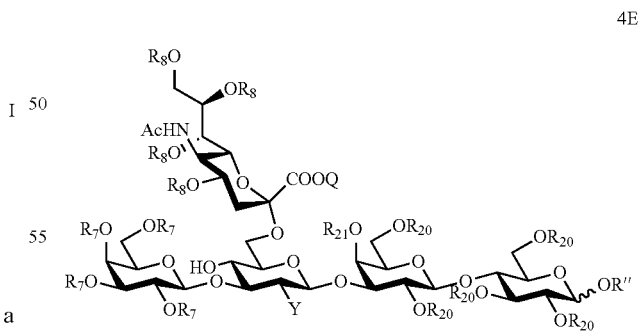

4E wherein R$_7$, R$_8$, R$_{20}$, R$_{21}$, Q and Y are as defined above, and

R" is a group removable by hydrogenolysis.

Other features of the invention will become apparent in view of the following exemplary embodiments which are illustrative but not limiting of the invention.

EXAMPLES

Example 1

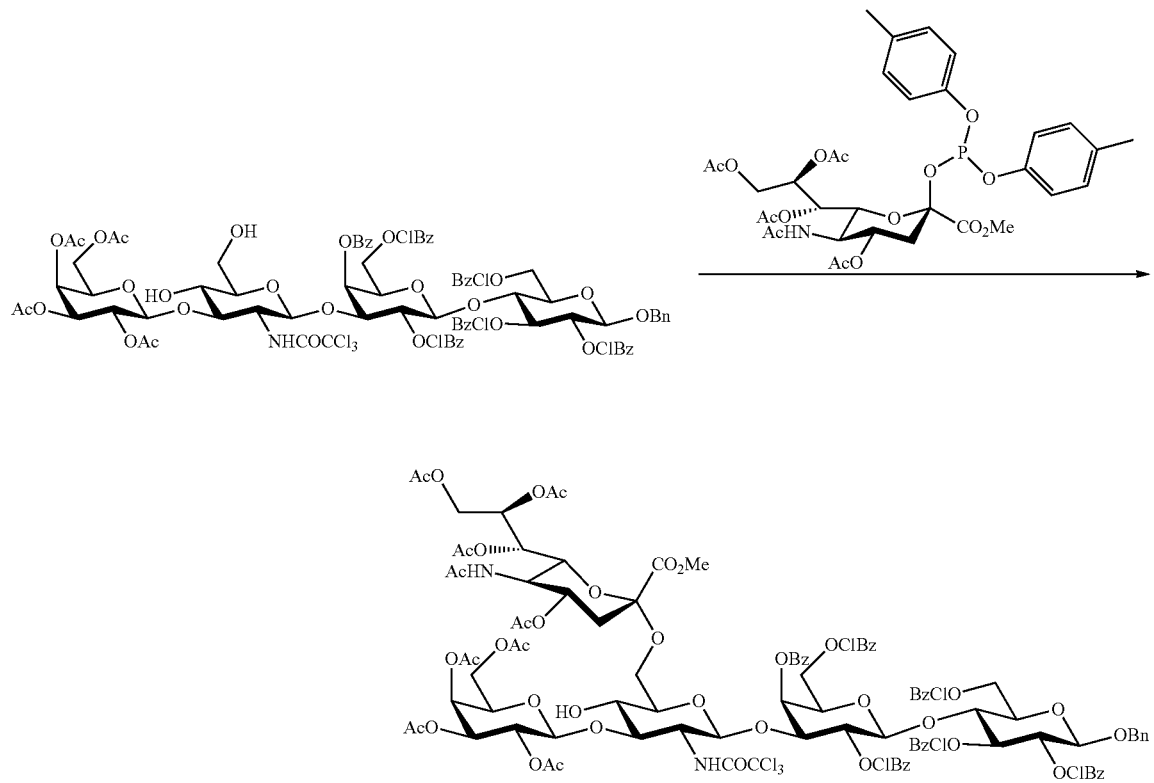

To a solution of the tetrasaccharide diol acceptor (10.0 g, ca. 93% purity, prepared as described in WO 2012/155916) and sialic acid phosphite donor (4.45 g, prepared as described in WO 2012/113404) in propionitrile (30 ml) was added trimethylsilyl triflate (0.4 ml) dropwise at −30° C. in the presence of 4 Å molecular sieves and the reaction mixture was allowed to warm up slowly to −20° C. and stirred at this temperature for 60 min. Extra amounts of the donor were added periodically (2.4 g+2.4 g+1.2 g) each followed by addition of TMSOTf (100 μl+100 μl+50 μl) every 60 min at −30° C. followed by stirring at −20° C. After 7 hours the mixture was quenched with EtOAc (50 ml) and sat. aq. NaHCO$_3$ (20 ml), stirred for 10 min at 0° C. and it was partitioned between EtOAc (150 ml total) and NaHCO$_3$ (100 ml), washed with 5% NaHCO$_3$ and brine. The combined aqueous solution was re-extracted with EtOAc (50 ml) and washed as above. The combined organic solution was dried and evaporated to give a white foam (20.4 g). The title product was isolated by flash chromatography on silica gel yielding 7.9 g of the title pentasaccharide (62%). LC-HRMS calculated for [C$_{103}$H$_{102}$Cl$_8$N$_2$O$_{43}$+H]$^+$ 2340.3412. found m/z 2340.3371 ([M+H]$^+$, rel. intensity 100%).

$^1$H NMR (CDCl$_3$, 300 MHz, CHCl$_3$=7.26) δ: 8.00-7.06 (m, 28H), 6.91-6.85 (m, 2H), 6.62 (d, 1H, J=7.1 Hz, NH), 5.64 (d, 1H, J=3.1 Hz), 5.56 (pt, 1H, J=9.7 Hz, J=9.1 Hz), 5.49-5.27 (m, 5H), 5.16 (bd, 1H, J=9.5 Hz), 5.09 (dd, 1H, J=8.0 Hz, J=10.6 Hz), 4.99-4.89 (m, 2H), 4.81-4.74 (m, 2H), 4.64 (d, 2H, J=8.0 Hz), 4.54 (d, 1H, 12.5 Hz), 4.40-4.33 (m, 3H), 4.31 (dd$_{po}$, 1H, J=2.6 Hz, J=12.6 Hz), 4.24 (dd, 1H, J=3.4 Hz, J=10.3 Hz), 4.16-3.94 (m, 8H), 3.88-3.79 (m, 3H), 3.76 (s$_o$, 3H, CO$_2$Me), 3.77-3.71 (m$_o$, 1H), 3.66 (pdt, 1H, J=3.6 Hz, J=10.6 Hz), 3.40-3.28 (m, 3H), 3.04 (pdt, 1H, J=7.7 Hz, J=9.8 Hz, H-2$_{glucN}$), 2.58 (dd, 1H, J=4.8 Hz, J=13.2 Hz, H-3a$_{sial}$), 2.12 (s, 3H), 2.11 (s, 6H), 2.02 (s$_o$, 3H), 2.01 (s$_o$, 3H), 1.99 (pt$_o$, 1H, H-3b$_{sial}$) 1.98 (s$_o$, 3H), 1.93 (s, 3H), 1.91 (s, 3H), 1.89 (s, 3H).

$^{13}$C NMR (CDCl$_3$, 75 MHz) δ: 171.3, 171.1, 170.6, 170.5, 170.4 (3C), 170.3, 169.5, 168.5, 165.3, 165.2, 165.1, 164.8, 164.6, 164.0, 161.8, 140.5, 140.3 (2C), 140.2, 139.8, 138.2, 136.6, 133.8, 131.7-127.6 (33C), 125.6, 101.2, 100.8, 99.2, 99.0, 98.2, 92.0, 81.2, 76.0, 75.1 (2C), 73.3 (2C), 72.6, 72.4, 72.0 (2C), 71.3, 71.0, 70.9, 70.4, 69.4, 69.2, 68.8, 68.7, 67.5, 67.0, 64.4, 63.2, 62.7, 62.5, 61.3, 58.9, 53.1, 48.8, 37.3, 23.6, 21.8, 21.5, 21.2-20.8 (6C).

Example 2

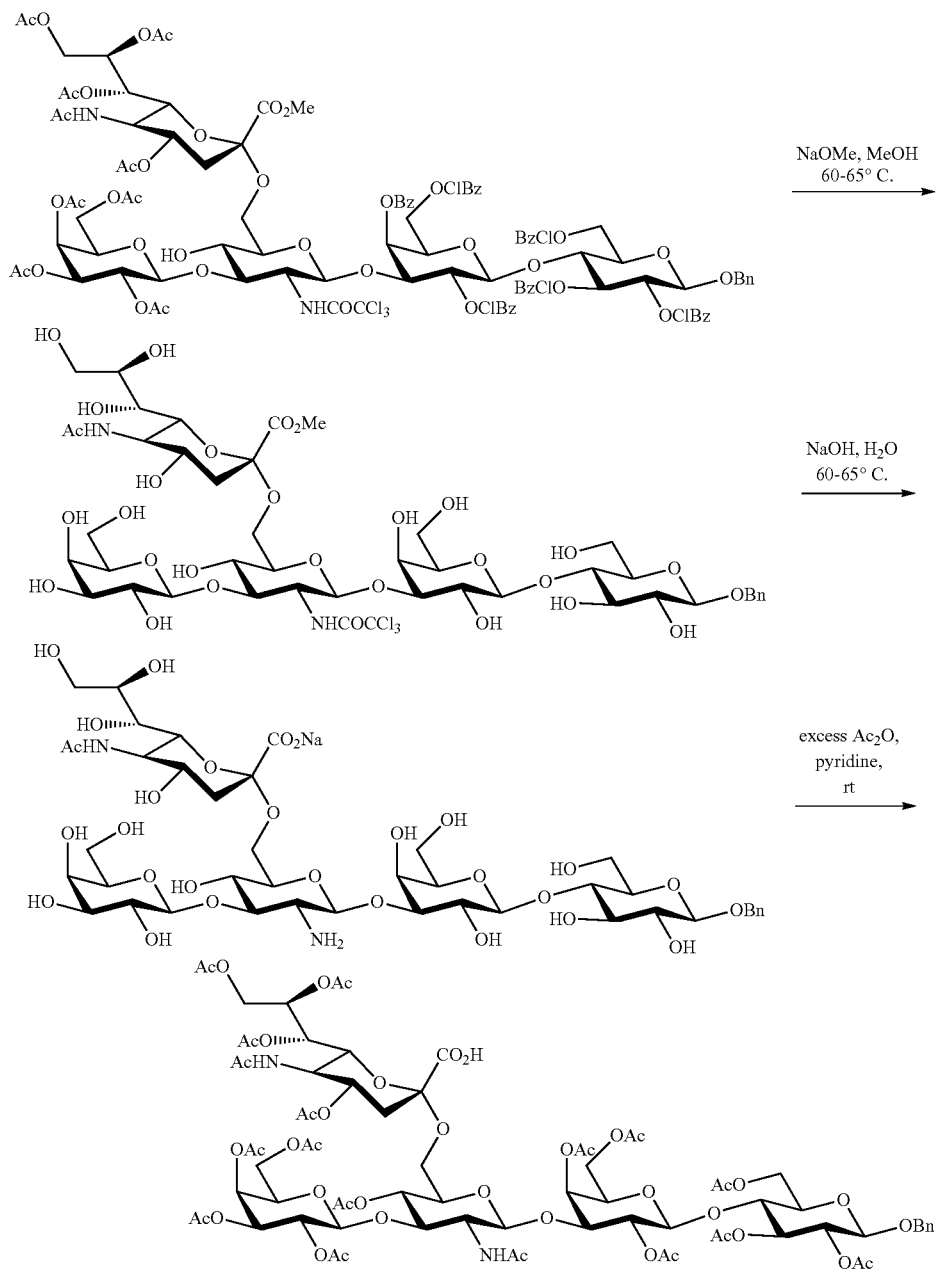

A solution of the product obtained according to Example 1 (13.18 g) in dry MeOH (65 ml) was treated with 25% (w/w) methanolic MeONa (1.05 ml) at 65° C. The mixture was stirred at this temperature for 3 h. The reaction mixture was neutralized by addition of AcOH and the obtained solution was concentrated to approx. 1/10 volume. The resulting solution was taken up in water and hexane. Layers were separated and the aqueous layer was washed twice with hexane. The water-MeOH phase was then concentrated to approx. 250 ml and treated with a 50% aqueous NaOH solution (2.6 ml) at 65° C. for 1.5 h. The reaction mixture was then evaporated in vacuo. The residue was taken up in dry pyridine (200 ml) and acetic anhydride (160 ml) and the mixture was stirred under for 40 hours. Volatiles were evaporated and coevaporated twice with toluene. The residue was taken up in $CH_2Cl_2$, washed with 5% aqueous HCl, then twice with brine. The organic phase was dried, filtered and concentrated. The residue was purified by flash chromatography to give the peracetylated compound (7.86 g, 81%) as a beige solid. LC-HRMS m/z 860.2636 [M+2H]$^{2+}$, 871.2552 [M+H+Na]$^{2+}$, 879.2423 [M+H+K]$^{2+}$.

$^1$H NMR (DMSO-d6, 300 MHz) δ: 7.66 (d, 1H, J=11.6 Hz, NH), 7.58 (d, 1H, J=8.9 Hz, NH), 7.39-7.21 (m, 5H), 5.31-5.01 (m, 5H), 4.91-4.47 (m, 9H), 4.41-3.27 (m, 23H), 2.52 (dd$_o$, 1H, J=5.2 Hz, H-3a$_{sial}$), 2.09 (s, 6H), 2.04 (s, 6H), 2.02 (s, 6H), 1.98 (s, 6H), 1.96 (s, 3H), 1.95 (s, 3H), 1.94 (s, 3H), 1.92 (s, 3H), 1.89 (s, 6H), 1.87 (s, 3H), 1.81 (s, 3H), 1.62 (s, 3H), 1.33 (pt, 1H, J=11.8 Hz, J=11.1 Hz, H-3b$_{sial}$).

Example 3

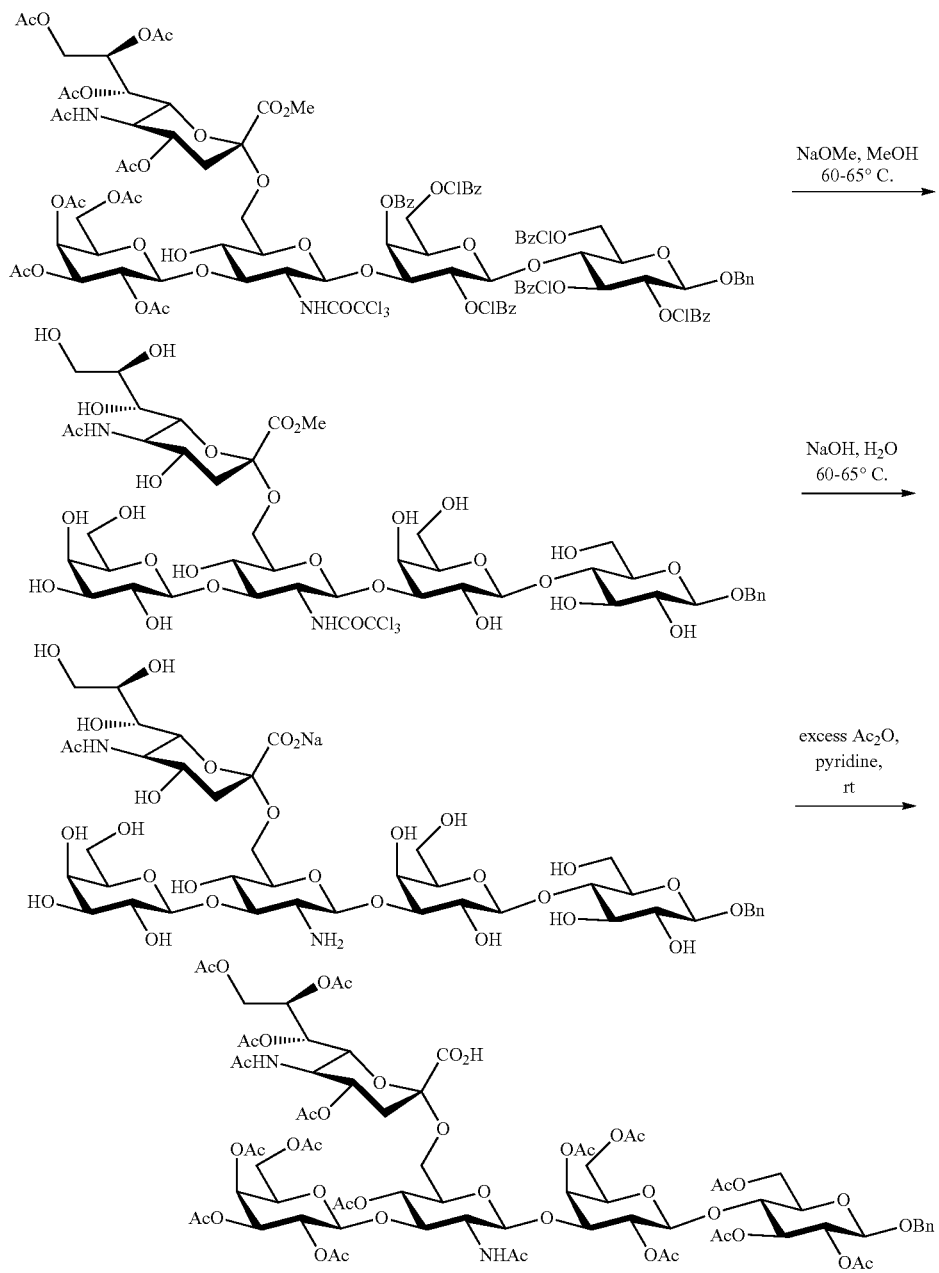

Step 1. A solution of the compound from example 1 (6.57 g) in dry MeOH (50 ml) was treated with 25% (w/w) methanolic MeONa (0.5 ml) and stirred at r.t. for 21 hours, quenched with AcOH and evaporated in vacuo. The obtained residue (6.14 g) was sonicated with $Et_2O$ and filtered (5×40 ml). Alternatively, methyl benzoates could be extracted by partitioning between water and organic solvent such as ether or hexane. The compound was dried in vacuum oven to give 3.90 g of a crude material.

Step 2. The obtained solid from step 1 was taken up in water (30 ml) containing NaOH (0.514 g) and stirred at r.t. for 3 days and then at 60° C. for 2 hrs. The mixture was neutralized with AcOH and extracted with ether. The aqueous phase gave 5.52 g of solid after evaporation. LC-HRMS calc. for $[C_{42}H_{66}N_2O_{28}-H]^-$ 1045.3729. found 1045.3732 ($[M-H]^-$).

Step 3. The product from step 2 was taken up in pyridine and $Ac_2O$ mixture (50 ml each) and stirred at 50° C. for 30 min then at r.t. for 18 hours. Extra amount of acetic anhydride (20 ml) was added and the mixture was stirred at 40° C. for 2 hours. The volatiles were removed in vacuo and the residue was coevaporated with toluene then partitioned between $CH_2Cl_2$ (200 ml) and 0.5 M HCl (50 ml). The aqueous phase was re-extracted with $CH_2Cl_2$ (3×20 ml). Combined organic solution was dried and evaporated to give 5.0 g of crude product as white solid. It was chromatographed on silica to give 3.89 g of the title compound (80.5%).

Example 4

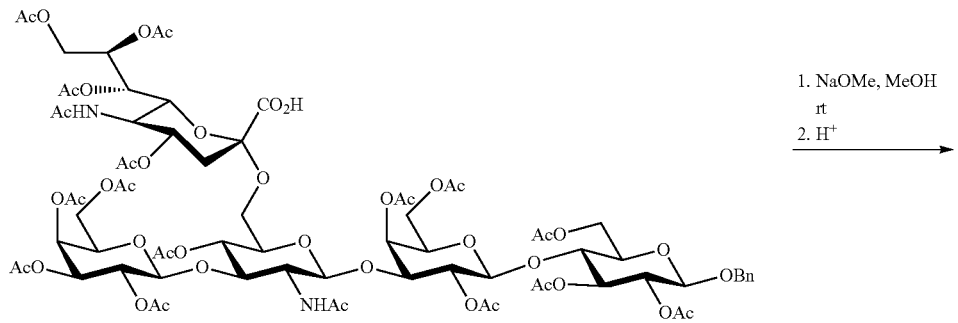

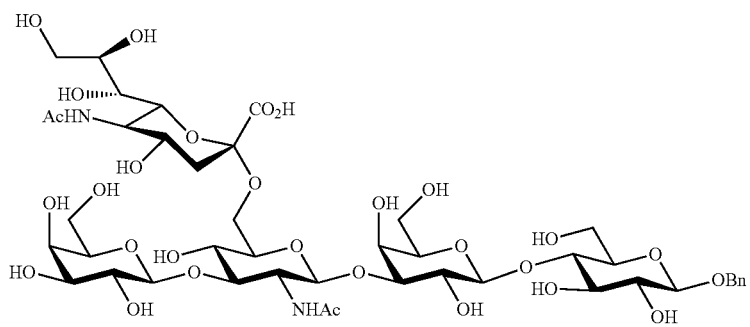

To a stirred solution of the compound according to Examples 2 or 3 (4.89 g) in dry MeOH (60 ml) was added 25% (w/w) methanolic MeONa (2.02 ml). After 16 hours the reaction mixture was neutralized carefully by addition of Dowex 50W-X8 resin (H$^+$-form) resin to pH=3. The suspension was filtered and the solvents were evaporated to give the title compound (3.05 g, 98%) as a white solid. LC-HRMS calc. for [$C_{44}H_{68}N_2O_{29}$—H]$^-$ 1087.3835. found 1087.3848 ([M−H]$^-$).

$^1$H NMR (D$_2$O, 300 MHz) δ: 7.46-7.35 (m, 5H), 4.89 (d, 1H, J=11.6 Hz, H$_{Bn}$), 4.71 (d, 1H, J=11.6 Hz, H$_{Bn}$), 4.65 (d, 1H, J=8.40 Hz), 4.51 (d, 1H, J=8.0 Hz), 4.39 (d, 1H, J=7.6 Hz), 4.38 (d, 1H, J=7.8 Hz), 4.12 (d, 1H, J=3.1 Hz), 3.99-3.44 (m, 29H), 3.30 (pt, 1H, J=8.5 Hz), 2.69 (dd, 1H, J=4.6 Hz, J=12.7 Hz, H-3a$_{sial}$), 1.99 (s, 3H), 1.98 (s, 3H), 1.68 (pt, 1H, J=11.3 Hz, J=12.3 Hz, H-3b$_{sial}$)

$^{13}$C NMR (D$_2$O, 75 MHz) δ: 175.6, 175.5, 173.5, 137.1, 129.4 (2C), 129.3 (2C), 129.1, 104.1, 103.6, 103.3, 101.6, 100.4, 82.9, 82.5, 79.0, 75.9, 75.6, 75.4, 75.1, 74.3, 73.4, 73.3, 73.1, 72.2 (2C), 71.3, 71.1, 70.6, 69.2, 69.0, 68.9, 68.7, 63.4, 63.3, 61.7, 60.7, 55.4, 52.5, 49.5, 40.5, 22.9, 22.7.

Example 5

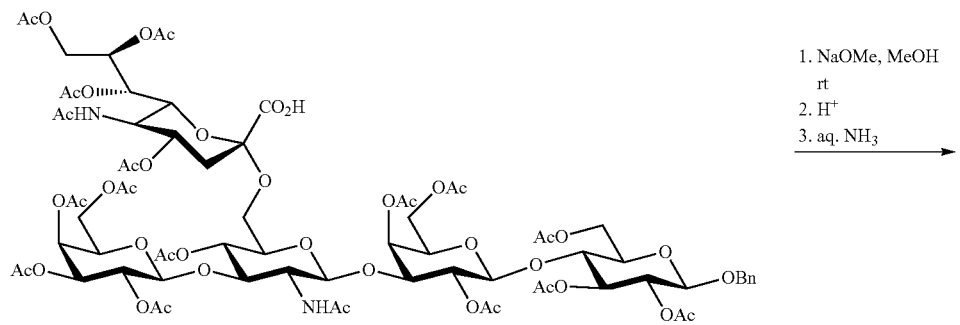

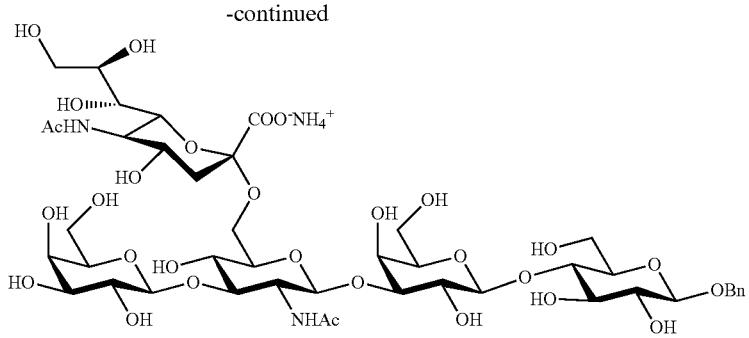

To a stirred solution of the compound according to Examples 2 or 3 (7.77 g) in dry MeOH (95 ml) was added 25% (w/w) methanolic MeONa (2.12 ml). After 16 hours the reaction mixture was neutralized carefully by addition of Dowex 50W-X8 resin ($H^+$-form) to pH=3. The suspension was filtered and 25% aq. $NH_3$ (1.5 ml) was added to the filtrate. The volatiles were then evaporated to give the ammonium salt (5.0 g, 100%) as a white solid.

Example 6

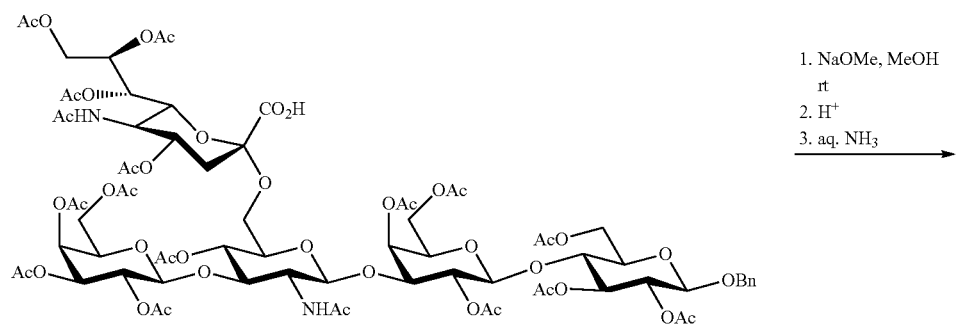

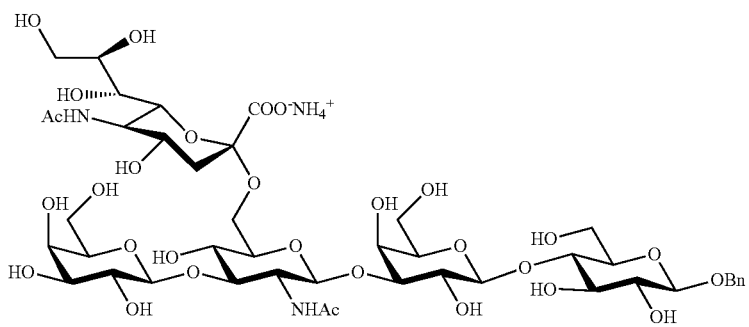

To a stirred solution of the compound according to Examples 2 or 3 (3.83 g) in dry MeOH (100 ml) was added 25% (w/w) methanolic MeONa (0.5 ml) to give a neutral pH. Extra amount of MeONa added (0.5 ml) to give a strongly basic pH. After 13 hours at r.t. the reaction mixture was neutralized carefully by addition of Dowex 50W-X8 resin ($H^+$-form) to pH=3. The suspension was filtered and 25% aq. $NH_3$ (1.0 ml) was added to the filtrate. The volatiles were then evaporated to give the ammonium salt (2.50 g, 100%).

Example 7

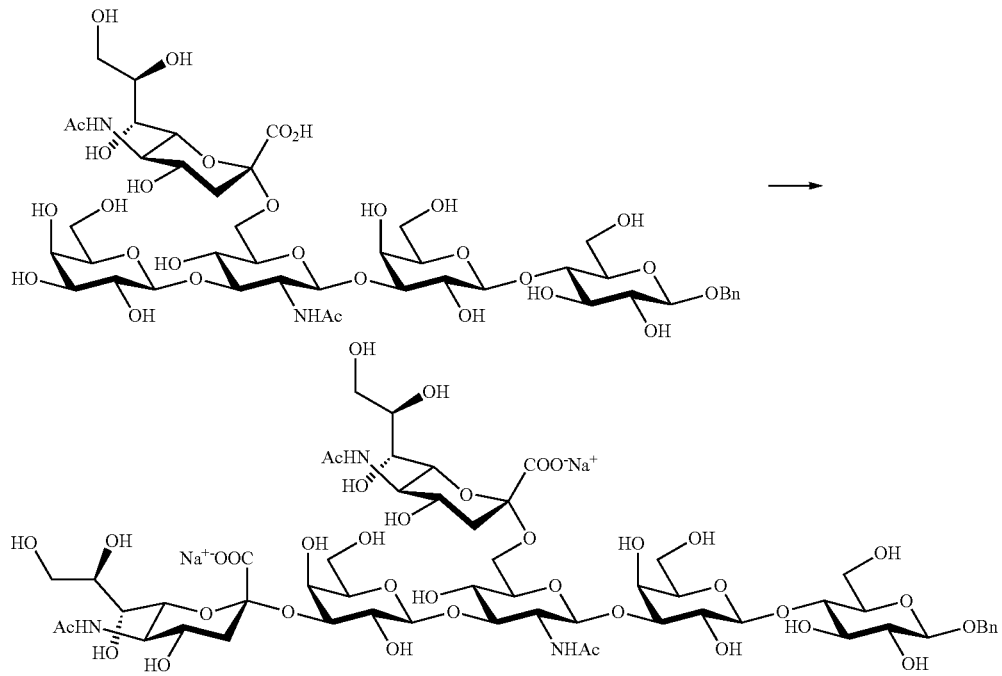

In parallel experiments, a solution of 3'-O-sialyllactose (300 mM) or p-nitrophenyl N-acetyl-α-neuraminoside (150 mM) as donors and the compound according to Example 4 as acceptor (100 mM) was incubated in incubation buffer tris-HCl (100 mM) at pH 7.0 with the recombinant transsialidase from *Trypanosoma cruzi* (Agusti et al. *Glycobiology* 14, 659 (2004) and Neubacher et al. *Org. Biomol. Chem.* 3, 1551 (2005)). The reaction mixtures were stirred at 20° C. for 24 hours and the conversion of the acceptor to the desired product was determined by HPLC. Conversion yield was estimated to be from 70 to 80% when using 3'-O-sialyllactose or from 40 to 50% when using p-nitrophenyl N-acetyl-α-neuraminoside.

Reaction mixtures were loaded on a Dowex 1 ($HCO_3^-$-form) column. After washing with distilled water, the monoacidic compounds (3'-O-sialyllactose or sialic acid and the remaining acceptor) were eluted with a 60 mM $NaHCO_3$ solution. The product was then eluted with a 125 mM $NaHCO_3$ solution. The eluted fractions containing acidic oligosaccharides were analysed by HPLC and pooled. The $NaHCO_3$ was removed by treating with Amberlite IR120 ($H^+$ form) until pH 3.0 was reached. The pH was then adjusted to 6.0 with NaOH. The mono-acidic fractions were freeze-dried and reused with another enzymatic run. The fractions containing the products were freeze-dried.

LC-HRMS: m/z calc. for $[C_{55}H_{85}N_3O_{37}-H]^-$ 1378.4789. found 1378.4807 $([M-H]^-)$, calc. for $[M-2H]^{2-}$ 688.7358. found 688.7376 (main peak).

$^1$H NMR (300 MHz, 100 mg in 0.7 ml $D_2O$, DHO=4.81 ppm) δ: 7.37-7.47 (m, 5H, Ph of Bn), 4.923 (d, J=11.6 Hz, 1H, $CH_2$ of Bn), 4.739 (d, J=11.5 Hz, 1H, $CH_2$ of Bn), 4.685 (d, J=8.4 Hz, 1H), 4.534 (d, J=8.0 Hz, 1H), 4.494 (d, J=7.8 Hz, 1H), 4.419 (d, J=7.7 Hz, 1H), 4.154 (d, J=3.1 Hz, 1H, H-4'), 4.074 (dd, J=3.1 Hz, J=9.8 Hz, 1H, H-3'''), 3.48-4.02 (overlapping m, 35H), 3.921 (overlapping d, J=3.2 Hz, H-4'''), 3.335 (t, J=8.35 Hz, 1H, H-2), 2.731 and 2.748 (two overlapping dd, J=12.5 Hz, J=4.9 Hz, 2H, two H-3''''$_{eq(2,6)\ and\ (2,3)}$), 2.01 (three overlapping s, 9H, 3 AcNH), 1.775 (t, J=12.1 Hz, 1H, H-3''''$_{ax(2,3)}$), and 1.679 (t, J=12.1 Hz, 1H, H-3''''$_{ax(2,6)}$).

$^{13}$C NMR (75 Hz, NaOAc=182.02 & 23.95 ppm) δ: 175.80, 175.73, 175.65 (3 Ac), 174.70 (C-1''''$_{(2-3)}$), 174.23 (C-1'''$_{(2-6)}$), 137.29 (C-1 of Ph), 129.58, 129.53 (C-2 & C-3 of Ph), 129.30 (C-4 of Ph), 104.19, 103.70, 103.37 (C-1''', C-1', C-1''), 101.77 (C-1), 100.96 (C-2''''$_{(2,6)}$), 100.41 (C-2''''$_{(2,3)}$), 83.07 (C-3''), 82.55 (C-3'), 79.17 (C-4), 76.37 (C-3'''), 75.87 (C-5'''), 75.75 (C-5'), 75.58 (C-5), 75.19 (C-3), 74.50 (C-5''), 73.57 (C-6''''$_{(2-3)}$), 73.28 (C-6''''$_{(2-6)}$), 72.62 (C-8'''$_{(2-3)}$), 72.50 (C-8'''$_{(2-6)}$), 72.30 ($CH_2$ of Bn), 70.74 (C-2'), 69.89 (C-2'''), 69.15, 69.14, 69.11, 69.00, 68.80 (overlapping C-4', C-4'', C-4''''$_{(2-6)\&(2-3)}$, C-7''''$_{(2-6)\&(2-3)}$), 68.07 (C-4'''), 63.60 (C-6''), 63.36 (C-9''''$_{(2,3)}$), 63.21 (C-9''''$_{(2,6)}$), 63.86 (overlapping C-6', C-6'''), 60.83 (C-6), 53.39 (C-2''), 52.63 (C-5''''$_{(2,6)}$), 52.43 (C-5''''$_{(2,3)}$), 40.86 (C-3'''$_{(2,6)}$), 40.53 (C-3'''$_{(2,3)}$), 23.12 (Ac of GlcNAc), 22.88 & 22.86 (2 overlapping Ac of $NeuAc_{(2-6)\&(2-3)}$).

Example 8: DS-LNT Disodium Salt

The compound obtained according to Example 7 (4.43 g) and 10% Pd on carbon (0.4 g) were suspended in a mixture of deionized water (15 ml) and methanol (15 ml) and stirred under hydrogen at 5 bar pressure. After 24 hours extra amount of the catalyst (100 mg) was added and the hydrogenolysis continued at 5 bars for 3 days. The reaction mixture was filtered via a short plug of Celite (5 g), which was further washed with 1:1 aqueous methanol and concentrated under reduced pressure to a small volume. The residue was treated with Amberlite IRC-86 ($H^+$ form). The obtained solution was passed through Amberlite IRC-86 column ($Na^+$ form). After all the product was eluted with water, it was freeze-dried to give the title disodium salt as a white foam (3.855 g, 93%). LC-MS: UV purity 97.2% (205 nm); the retention time and MS/MS were identical with those of a reference sample purchased from Carbosynth. HRMS, m/z calculated for $[C_{48}H_{79}N_3O_{37}-2H]^{2-}$ 643.7123. found 643.7150 ($[M-2H]^{2-}$). $^1H$ NMR (300 MHz, $D_2O$) was identical within 0.01 ppm with that reported in the literature for DS-LNT (Sabesan et al. *J. Am. Chem. Soc.* 108, 2068 (1986)).

Example 9: LST b Sodium Salt

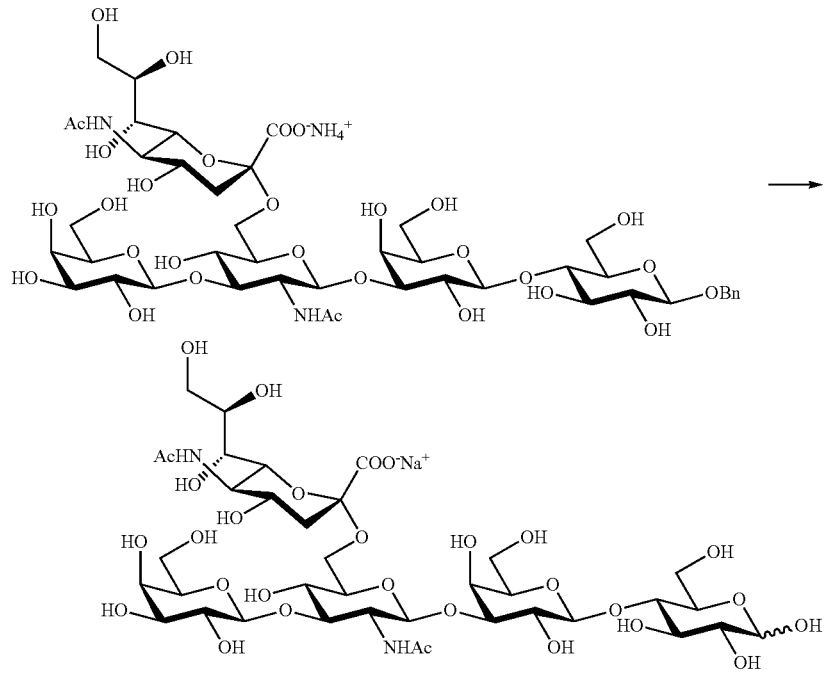

The compound according to example 5 or 6 (200 mg) was hydrogenolised at 5 bar in the presence of 10% Pd on charcoal (40 mg) in 1:1 methanol-water mixture (20 ml) until full conversion as monitored by TLC. The obtained reaction mixture was filtered, passed through Dowex 50WX4 resin ($Na^+$ form, 10 g), fractions containing the product were concentrated and freeze-dried to give 178 mg of white foam. HRMS: m/z calc. for $[C_{37}H_{61}N_2O_{29}-H]^-$ 997.3360. found 997.3269 ($[M-H]^-$). The $^1H$ NMR spectrum was identical to that of the literature for LST b (Sabesan et al. *J. Am. Chem. Soc.* 108, 2068 (1986)).

The invention claimed is:

1. A method for making a 3-O-galactosyl-GlcNAc or -GalNAc derivative of formula 1 and salts thereof

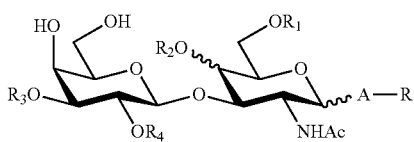

wherein

R is selected from the group consisting of —OH, —$N_3$, and —$OR_6$, wherein $R_6$ is selected from the group consisting of allyl optionally substituted by one or more methyl, propargyl optionally substituted by one or more methyl, 2-trimethylsilyl-ethyl, —$(CH_2)_n$—$NH_2$, and —$(CH_2)_n$—$N_3$, wherein integer n is 1 to 10;

$R_1$ is a sialyl moiety or —$CH(R_5)$—COOH, wherein $R_5$ is selected from the group consisting of H, alkyl, and benzyl;

$R_2$ is H or a fucosyl moiety;

$R_3$ is H or a sialyl moiety;

$R_4$ is H or a fucosyl moiety, provided that at least one of $R_3$ and $R_4$ is H; and A is a divalent carbohydrate linker;

comprising the steps:

a) sialylation or addition of a —$HC(R_5)$-COOH group of a compound of formula 2

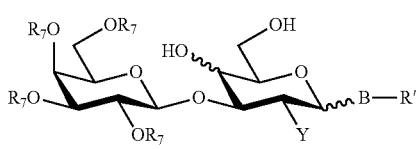

wherein

R' is —$N_3$ or —$OR'_6$, wherein $R'_6$ is selected from the group consisting of allyl optionally substituted by one or more methyl, propargyl optionally substituted by one or more methyl, a group removable by hydrogenolysis, 2-trimethylsilyl-ethyl, and —$(CH_2)_n$—$N_3$, wherein integer n is 1 to 10;

$R_7$ is independently acyl;

Y is selected from the group consisting of —NHAc, haloalkanoylamido, —$NAc_2$, haloalkoxycarbonylamino, 2,3-diphenylmaleimido, 2,3-dimethylmaleimido, and —$N_3$; and B is divalent carbohydrate linker in protected form;

b) optional fucosylation of the compound obtained in step a);

c) de-O-acylation and/or basic hydrolysis, optional mild acidic hydrolysis and optional transformation of Y to —NHAc of the compound obtained in step a) or step b);

d) optional sialylation or fucosylation of the compound obtained in step c); and e) optional catalytic hydrogenolysis and/or anomeric deprotection of the compound obtained in step d).

2. The method according to claim 1, wherein sialylation or addition of a —HC(R$_5$)-COOH group of the compound of formula 2 in step a) results in the formation of a compound of formula 4

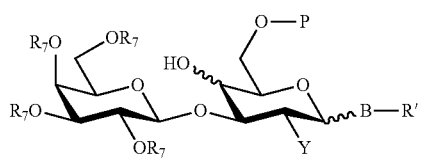

4 wherein

R' is —N$_3$ or —OR'$_6$, wherein R'$_6$ is selected from the group consisting of allyl optionally substituted by one or more methyl, propargyl optionally substituted by one or more methyl, a group removable by hydrogenolysis, 2-trimethylsilyl-ethyl, and —(CH$_2$)$_n$—N$_3$, wherein integer n is 1 to 10;

R$_7$ is independently acyl;

Y is selected from the group consisting of —NHAc, haloalkanoylamido, —NAc$_2$, haloalkoxycarbonylamino, 2,3-diphenylmaleimido, 2,3-dimethylmaleimido, and —N$_3$;

B is divalent carbohydrate linker in protected form; and

P is a protected sialyl moiety or —CH(R$_5$)—COOR$_{10}$, wherein R$_5$ is selected from the group consisting of H, alkyl, and benzyl, and R$_{10}$ is alkyl or benzyl.

3. The method according claim 2, wherein the sialylation in step a) is carried out by reacting the compound of formula 2 with a compound of formula 3

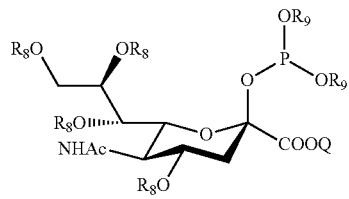

3 wherein

R$_8$ is acyl;

Q is alkyl or benzyl; and

R$_9$ is optionally substituted phenyl or benzyl;

to give a compound of formula 4A

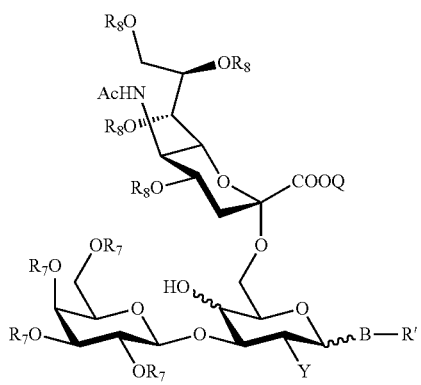

4A wherein

R' is —N$_3$ or —OR'$_6$, wherein R'$_6$ is selected from the group consisting of allyl optionally substituted by one or more methyl, propargyl optionally substituted by one or more methyl, a group removable by hydrogenolysis, 2-trimethylsilyl-ethyl, and —(CH$_2$)$_n$—N$_3$, wherein integer n is 1 to 10;

R$_7$ is independently acyl;

Y is selected from the group consisting of —NHAc, haloalkanoylamido, —NAc$_2$, haloalkoxycarbonylamino, 2,3-diphenylmaleimido, 2,3-dimethylmaleimido, and —N$_3$.

4. The method according to claim 3, wherein the compound of formula 4A is a compound of formula 4E

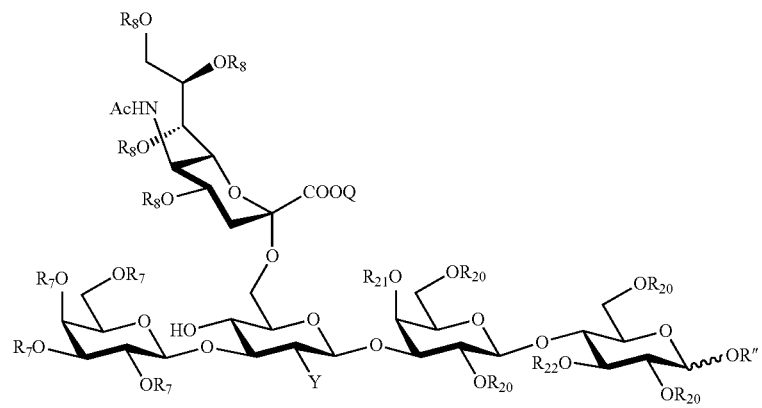

4E wherein

R" is a group removable by hydrogenolysis;

Y is selected from the group consisting of —NHAc, haloalkanoylamido, —NAc$_2$, haloalkoxycarbonylamino, 2,3-diphenylmaleimido, 2,3-dimethylmaleimido, and azido;

R$_7$ is independently acyl;

R$_8$ is independently acyl;

R$_{20}$ is independently acyl;

R$_{21}$ is H or acyl; and

Q is alkyl or benzyl.

5. The method according to claim 1, wherein the optional fucosylation in step b) comprises the reaction of a compound of formula 4

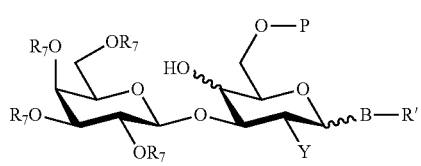

wherein

R' is —N$_3$ or —OR'$_6$, wherein R'$_6$ is selected from the group consisting of allyl optionally substituted by one or more methyl, propargyl optionally substituted by one or more methyl, a group removable by hydrogenolysis, 2-trimethylsilyl-ethyl, and —(CH$_2$)$_n$—N$_3$, wherein integer n is 1 to 10;

R$_7$ is independently acyl;

Y is selected from the group consisting of —NHAc, haloalkanoylamido, —NAc$_2$, haloalkoxycarbonylamino, 2,3-diphenylmaleimido, 2,3-dimethylmaleimido, and —N$_3$;

B is divalent carbohydrate linker in protected form; and

P is a protected sialyl moiety or —CH(R$_5$)—COOR$_{10}$, wherein R$_5$ is selected from the group consisting of H, alkyl, and benzyl, and R$_{10}$ is alkyl or benzyl;

with a compound of formula 5

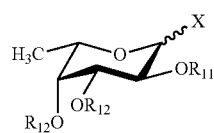

wherein

X is selected from the group consisting of a halogen, —OC(=NH)CCl$_3$, —O-pentenyl, —OAc, —OBz, and —SR$_{13}$, wherein R$_{13}$ is alkyl or optionally substituted phenyl;

R$_{11}$ is acyl or a group removable by hydrogenolysis; and

R$_{12}$ is a group removable by hydrogenolysis, acyl, or two R$_{12}$ groups together that form a moiety

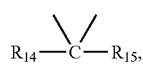

wherein R$_{14}$ and R$_{15}$ independently are alkyl or phenyl, or wherein R$_{14}$ and R$_{15}$ together with the carbon atom, to which they are attached, form a cycloalkylidene;

to give a compound of formula 6

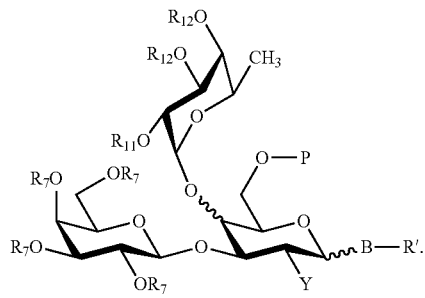

6. The method according to claim 5, wherein the compound of formula 4 is a compound of formula 4E

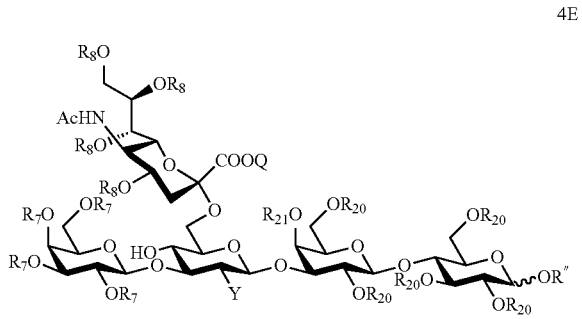

wherein

R" is a group removable by hydrogenolysis;

Y is selected from the group consisting of —NHAc, haloalkanoylamido, —NAc$_2$, haloalkoxycarbonylamino, 2,3-diphenylmaleimido, 2,3-dimethylmaleimido, and azido;

R$_7$ is independently acyl;

R$_8$ is independently acyl;

R$_{20}$ is independently acyl;

R$_{21}$ is H or acyl; and

Q is alkyl or benzyl; and the compound of formula 5 is a compound of formula 5A

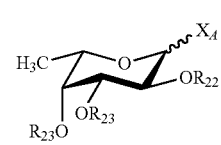

wherein

X$_A$ is alkylthio or optionally substituted phenylthio;

R$_{22}$ and R$_{23}$ are, independently, a group removable by hydrogenolysis or acyl; and the compound formula 6 is a compound of formula 6E

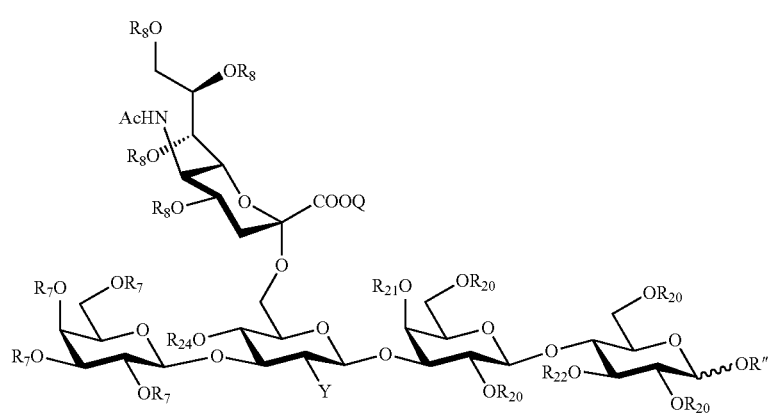

wherein
R'' is a group removable by hydrogenolysis;
Y is selected from the group consisting of —NHAc, haloalkanoylamido, —NAc$_2$, haloalkoxycarbonylamino, 2,3-diphenylmaleimido, 2,3-dimethylmaleimido, and azido;
R$_7$ is independently acyl;
R$_8$ is independently acyl;
R$_{20}$ is independently acyl;
R$_{21}$ is H or acyl; and
Q is alkyl or benzyl; and
R$_{24}$ is moiety I

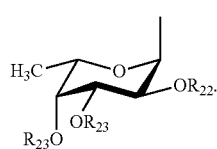

7. The method according to claim 1, wherein the compound obtained in step a) or step b) is converted into a compound of formula 7

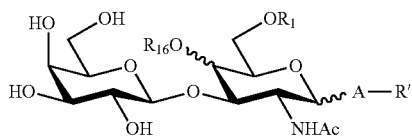

wherein
R' is —N$_3$ or —OR'$_6$, wherein R'$_6$ is selected from the group consisting of allyl optionally substituted by one or more methyl, propargyl optionally substituted by one or more methyl, a group removable by hydrogenolysis, 2-trimethylsilyl-ethyl, and —(CH$_2$)$_n$—N$_3$, wherein integer n is 1 to 10;
R$_1$ is a sialyl moiety or —CH(R$_5$)—COOH, wherein R$_5$ is selected from the group consisting of H, alkyl, and benzyl;
moiety A is a divalent carbohydrate linker in deprotected form; and
R$_{16}$ is H or a moiety of formula C

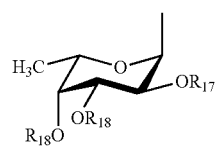

wherein
R$_{17}$ and R$_{18}$, independently, are H or a group removable by hydrogenolysis;
comprising the steps of:
i) base catalysed transesterification; and/or
ii) basic hydrolysis;
iii) optional mild acidic hydrolysis; and
iv) optional conversion to Y to —NHAc.

8. The method according to claim 4, wherein the compound of formula 4E is converted to a compound of formula 6E

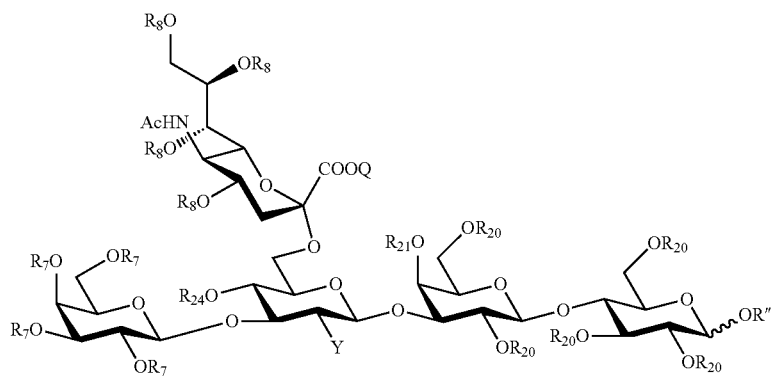

wherein

R'' is a group removable by hydrogenolysis;

Y is selected from the group consisting of —NHAc, haloalkanoylamido, —NAc$_2$, haloalkoxycarbonylamino, 2,3-diphenylmaleimido, 2,3-dimethylmaleimido, and azido;

R$_7$ is independently acyl;

R$_8$ is independently acyl;

R$_{20}$ is independently acyl;

R$_{21}$ is selected from the group consisting of H and acyl; and

Q is selected from the group consisting of alkyl and benzyl; and

R$_{24}$ is moiety I

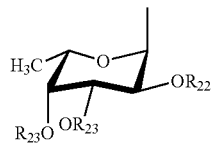

I wherein

R$_{22}$ and R$_{23}$ are, independently, a group removable by hydrogenolysis or acyl; and wherein the compound of formula 6E is subjected to deprotection and optional functional group transformation comprising:

i) base catalysed trans esterification deprotection;

ii) basic hydrolysis; and iii) where group Y in the compound of formula 4E or 6E is selected from the group consisting of haloalkanoylamido, haloalkoxycarbonylamino, 2,3-diphenylmaleimido, 2,3-dimethylmaleimido, and azido;

is deprotected to amino under the conditions used in step ii) followed by selective N-acetylation, or peracetylation followed by de-O-acetylation;

to yield a compound of formula 7B

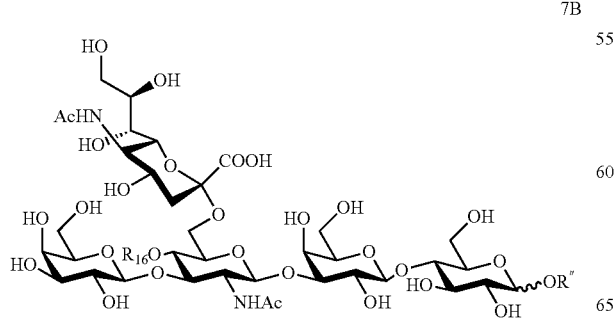

7B wherein

R'' is a group removable by hydrogenolysis; and

R$_{16}$ is H or moiety C

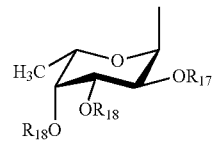

C wherein

R$_{17}$ and R$_{18}$, independently, are H or a group removable by hydrogenolysis.

9. The method according to claim 1, wherein a compound of formula 7 is obtained in step c)

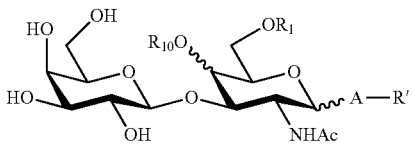

7 wherein

R' is —N$_3$ or —OR'$_6$, wherein R'$_6$ is selected from the group consisting of allyl optionally substituted by one or more methyl, propargyl optionally substituted by one or more methyl, a group removable by hydrogenolysis, 2-trimethylsilyl-ethyl, and —(CH$_2$)$_n$—N$_3$, wherein integer n is 1 to 10;

R$_1$ is a sialyl moiety or —CH(R$_5$)—COOH, wherein R$_5$ is selected from the group consisting of H, alkyl, and benzyl;

moiety A is a divalent carbohydrate linker in deprotected form; and

R$_{16}$ is H or a moiety of formula C

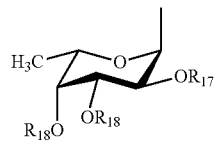

C wherein

R$_{17}$ and R$_{18}$, independently, are H or a group removable by hydrogenolysis;

and wherein the compound of formula 7 is optionally reacted with a sialyl donor in step d) under catalysis of an enzyme having α-2-3-transsialidase activity or with a fucosyl donor under catalysis of an enzyme having transfucosidase/fucosynthase activity to give a compound of formula 10

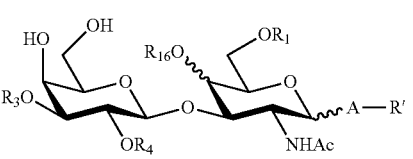

10 wherein

R₃ is H or a sialyl; and

R₄ is H or a fucosyl moiety, provided that one of R₃ and R₄ is H.

10. The method according to claim 9, wherein the compound of formula 7 is a compound of formula 7B

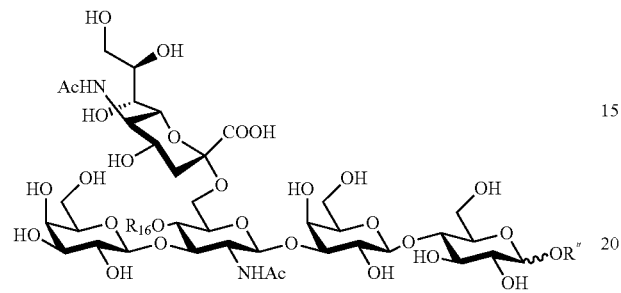

7B wherein

R" is a group removable by hydrogenolysis; and

R₁₆ is H or moiety C

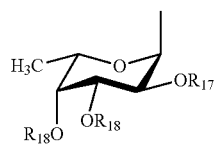

C wherein

R₁₇ and R₁₈ independently, are H or a group removable by hydrogenolysis;

the sialyl donor is 3'-O-sialyllactose or 2-O-(p-nitrophenyl) N-acetyl-α-neuraminoside; and the compound of formula 10 is a compound of formula 10D 11. The method according to claim 9, wherein the compound of formula 7 is a compound of formula 7B

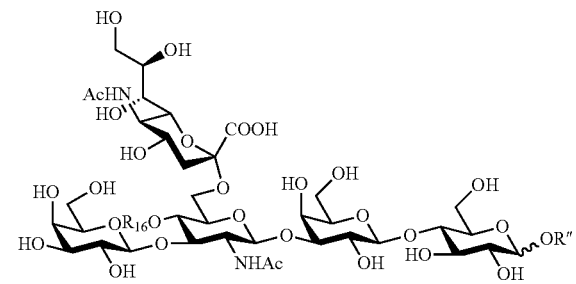

7B wherein

R" is a group removable by hydrogenolysis; and

R₁₆ is H or moiety C

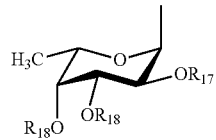

C wherein

R₁₇ and R₁₈, independently, are H or a group removable by hydrogenolysis;

the fucosyl donor is 2-O-fucosyllactose or fucosyl fluoride; and the compound of formula 10 is a compound of formula 10E

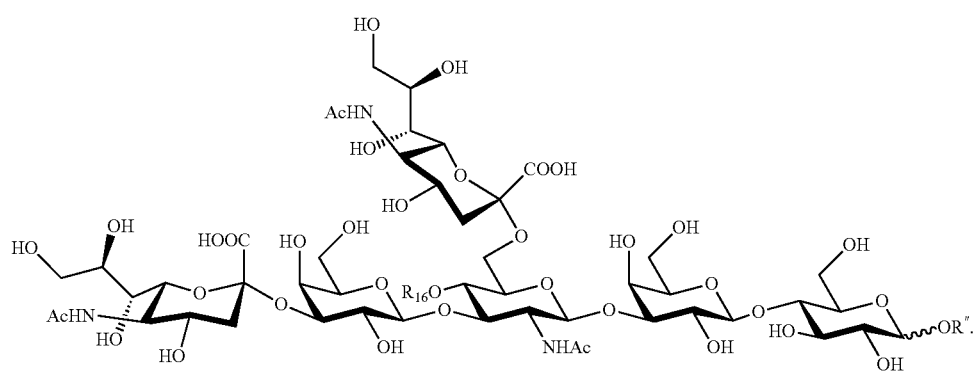

10D

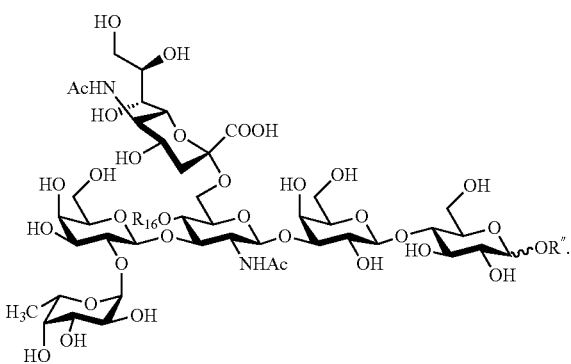

12. The method according to claim 1, wherein a compound of formula 10 is obtained in step d)

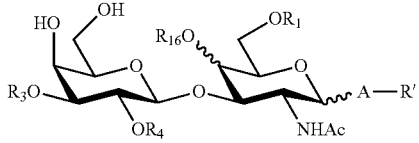

wherein
R' is —N$_3$ or —OR'$_6$, wherein R'$_6$ is selected from the group consisting of allyl optionally substituted by one or more methyl, propargyl optionally substituted by one or more methyl, a group removable by hydrogenolysis, 2-trimethylsilyl-ethyl, and —(CH$_2$)$_n$—N$_3$, wherein integer n is 1 to 10;
R$_1$ is a sialyl moiety or —CH(R$_5$)—COOH, wherein R$_5$ is selected from the group consisting of H, alkyl, and benzyl;
R$_{16}$ is H or a moiety of formula C

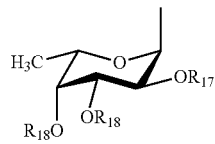

wherein
R$_{17}$ and R$_{18}$, independently, are H or a group removable by hydrogenolysis;
moiety A is a divalent carbohydrate linker in deprotected form;
R$_3$ is H or a sialyl; and
R$_4$ is H or a fucosyl moiety, provided that at least one of R$_3$ and R$_4$ is H;
wherein
the compound of formula 10 is subjected to catalytic hydrogenolysis and/or anomeric deprotection in the optional step e) to give the compound of formula 1

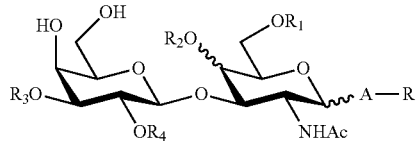

wherein
R is selected from the group consisting of —OH, —N$_3$, and —OR$_6$, wherein R$_6$ is selected from the group consisting of allyl optionally substituted by one or more methyl, propargyl optionally substituted by one or more methyl, 2-trimethylsilyl-ethyl, —(CH$_2$)$_n$—NH$_2$, and —(CH$_2$)$_n$—N$_3$, wherein integer n is 1 to 10;
R$_1$ is a sialyl moiety or —CH(R$_5$)—COOH, wherein R$_5$ is selected from H, alkyl, and benzyl;
R$_2$ is H or a fucosyl moiety;
R$_3$ is H or a sialyl moiety;
R$_4$ is H or a fucosyl moiety, provided that at east one of R$_3$ and R$_4$ is H; and
A is a divalent carbohydrate linker.

13. The method according to claim 12, wherein the compound of formula 10 is a compound of formula 10D

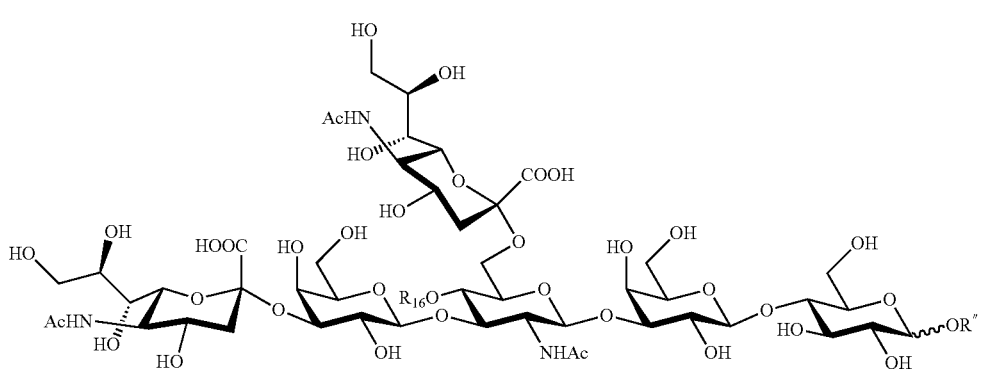

wherein
R" is a group removable by hydrogenolysis; and
$R_{16}$ is H or moiety C

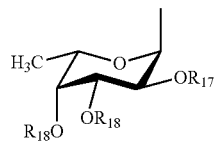

C wherein
$R_{17}$ and $R_{18}$, independently, are H or a group removable by hydrogenolysis; or
the compound of formula 10 is a compound of formula 10E

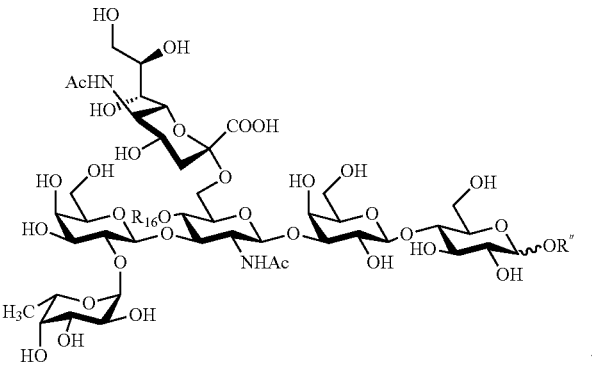

10E wherein
catalytic hydrogenolysis of a compound of formula 10E gives DS-LNT, FDS-LNT or F-LST b.

14. The method according to claim 12, wherein the compound of formula 10 is a compound of formula 7B

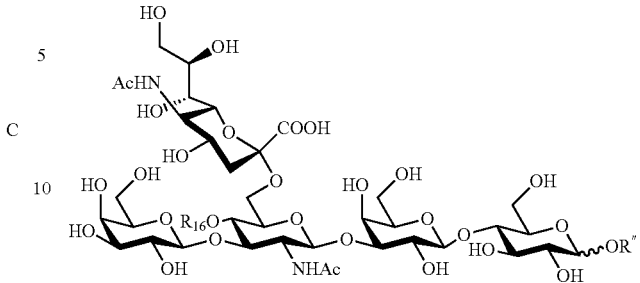

7B wherein
R" is a group removable by hydrogenolysis; and
$R_{16}$ is or moiety C

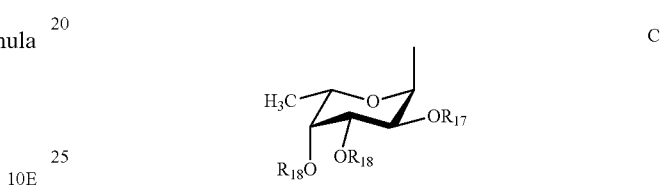

C wherein
$R_{17}$ and $R_{18}$, independently, are H or a group removable by hydrogenolysis; and
catalytic hydrogenolysis of the compound of formula 7B gives a compound of formula 1D

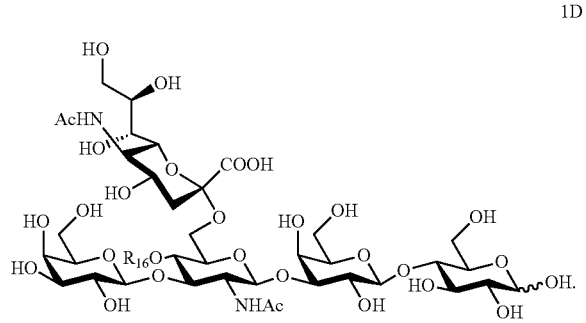

1D

* * * * *